US010405998B2

(12) United States Patent
Smith et al.

(10) Patent No.: US 10,405,998 B2
(45) Date of Patent: Sep. 10, 2019

(54) MOUNTING BRACKET FOR CONNECTING A PROSTHETIC LIMB TO A PROSTHETIC FOOT

(71) Applicant: Ability Dynamics, LLC, Tempe, AZ (US)

(72) Inventors: Keith B. Smith, Gilbert, AZ (US); Gene Parker, Mesa, AZ (US); James Scott, Phoenix, AZ (US); Brian Werner, Mesa, AZ (US)

(73) Assignee: Ability Dynamics LLC, Tempe, AZ (US)

(*) Notice: Subject to any disclaimer, the term of this patent is extended or adjusted under 35 U.S.C. 154(b) by 112 days.

(21) Appl. No.: 15/726,712

(22) Filed: Oct. 6, 2017

(65) Prior Publication Data

US 2018/0042737 A1    Feb. 15, 2018

Related U.S. Application Data

(63) Continuation-in-part of application No. 14/731,771, filed on Jun. 5, 2015, now abandoned, and a
(Continued)

(51) Int. Cl.
*A61F 2/66* (2006.01)
*A61F 2/50* (2006.01)
(Continued)

(52) U.S. Cl.
CPC ............... *A61F 2/66* (2013.01); *A61F 2/76* (2013.01); *A61F 2/60* (2013.01);
(Continued)

(58) Field of Classification Search
CPC ........................................................ A61F 2/76
See application file for complete search history.

(56) References Cited

U.S. PATENT DOCUMENTS

| 4,578,082 A | 3/1986 | Sen-Jang |
| 4,822,363 A | 4/1989 | Phillips |

(Continued)

FOREIGN PATENT DOCUMENTS

| CA | 2054588 | 5/1999 |
| CN | 2089799 U | 8/1990 |

(Continued)

OTHER PUBLICATIONS

Roland D. Christensen, U.S. Appl. No. 09/607,494 for "Prosthetic Foot," filed Jun. 30, 2000, abandoned Oct. 29, 2002.
(Continued)

*Primary Examiner* — Jacqueline Wozniki
(74) *Attorney, Agent, or Firm* — The Noblitt Group, PLLC

(57) ABSTRACT

A mounting bracket for a prosthetic foot configured to attach to a residual limb, comprising an upper member, a lower member and compression torsion joint. The upper member comprises an upper flange, a mating post, and mounting portion configured to attach to the residual limb. The lower member comprises a mating portion, a lower flange, and a mounting portion configured to attach to the prosthetic foot. The compression torsion joint couples the upper member to the lower member and is configured to limit the vertical movement and torsional movement of the upper member with respect to the lower member.

22 Claims, 34 Drawing Sheets

Related U.S. Application Data continuation-in-part of application No. 14/731,818, filed on Jun. 5, 2015, and a continuation of application No. 13/642,501, filed on Nov. 27, 2012, now Pat. No. 9,078,773, and a continuation of application No. 13/568,535, filed on Aug. 7, 2012, now abandoned, and a continuation of application No. 13/568,535, filed on Aug. 7, 2012, now abandoned, which is a continuation-in-part of application No. PCT/US2011/033319, filed as application No. PCT/US2011/003319 on Apr. 20, 2011, which is a continuation-in-part of application No. 12/799,215, filed on Apr. 20, 2010, now abandoned, which is a continuation of application No. 12/799,215, filed on Apr. 20, 2010, now abandoned, which is a continuation-in-part of application No. 11/901,845, filed on Sep. 19, 2007, now Pat. No. 8,048,173.

(60) Provisional application No. 62/539,743, filed on Aug. 1, 2017, provisional application No. 62/451,870, filed on Jan. 30, 2017, provisional application No. 62/407,954, filed on Oct. 13, 2016.

(51) Int. Cl.
*A61F 2/60* (2006.01)
*A61F 2/76* (2006.01)

(52) U.S. Cl.
CPC ............... *A61F 2002/5003* (2013.01); *A61F 2002/5007* (2013.01); *A61F 2002/5009* (2013.01); *A61F 2002/665* (2013.01); *A61F 2002/6614* (2013.01); *A61F 2002/6621* (2013.01); *A61F 2002/6642* (2013.01); *A61F 2002/6657* (2013.01); *A61F 2002/6664* (2013.01); *A61F 2002/6671* (2013.01); *A61F 2002/6692* (2013.01); *A61F 2230/0028* (2013.01)

(56) References Cited

U.S. PATENT DOCUMENTS

| | | |
|---|---|---|
| 5,062,859 A | 11/1991 | Naeder |
| 5,112,356 A | 5/1992 | Harris et al. |
| 5,116,382 A | 5/1992 | Wilson et al. |
| 5,156,632 A | 10/1992 | Wellershaus |
| 5,258,038 A | 11/1993 | Robinson et al. |
| 5,258,039 A | 11/1993 | Goh et al. |
| 5,352,189 A | 10/1994 | Schumann et al. |
| 5,443,522 A | 8/1995 | Hiemisch |
| 5,443,528 A | 11/1995 | Allen |
| 5,514,186 A | 5/1996 | Phillips |
| 5,653,767 A | 8/1997 | Allen et al. |
| 5,701,686 A | 12/1997 | Herr |
| 5,766,265 A | 6/1998 | Phillips |
| 5,888,239 A | 3/1999 | Wellershaus et al. |
| 5,897,594 A | 4/1999 | Martin et al. |
| 5,944,760 A | 8/1999 | Christensen |
| 5,954,075 A | 9/1999 | Gilmour |
| 5,993,488 A | 11/1999 | Phillips |
| 6,077,301 A | 6/2000 | Pusch |
| 6,099,572 A | 8/2000 | Mosler et al. |
| 6,120,547 A | 9/2000 | Christensen |
| 6,197,068 B1 | 3/2001 | Christensen |
| 6,241,776 B1 | 6/2001 | Christensen |
| 6,261,324 B1 | 7/2001 | Merlette |
| 6,406,500 B1 | 6/2002 | Phillips |
| 6,663,673 B2 | 12/2003 | Christensen |
| 6,669,737 B2 | 12/2003 | Mosler et al. |
| 6,702,858 B2 | 3/2004 | Christensen |
| 6,712,860 B2 | 3/2004 | Rubie et al. |
| 6,764,522 B1 | 7/2004 | Cehn |
| 6,767,370 B1 | 7/2004 | Mosler et al. |
| 6,805,717 B2 | 10/2004 | Christensen |
| 6,811,571 B1 | 11/2004 | Phillips |
| 6,852,131 B1 | 2/2005 | Chen et al. |
| 6,875,241 B2 | 4/2005 | Christensen |
| 6,875,242 B2 | 4/2005 | Christensen |
| 6,911,052 B2 | 6/2005 | Christensen |
| 6,929,665 B2 | 8/2005 | Christensen |
| 6,942,704 B2 | 9/2005 | Sulprizio |
| 6,966,933 B2 | 11/2005 | Christensen |
| 6,972,043 B1 | 12/2005 | Biedermann et al. |
| 7,063,727 B2 | 6/2006 | Phillips et al. |
| 7,172,630 B2 | 2/2007 | Christensen |
| 7,178,218 B1 | 2/2007 | Houser et al. |
| 7,341,603 B2 | 3/2008 | Christensen |
| 7,419,509 B2 | 9/2008 | Christensen |
| 7,462,201 B2 | 12/2008 | Christensen |
| 7,520,904 B2 | 4/2009 | Christensen |
| 7,572,299 B2 | 8/2009 | Christensen |
| 7,578,852 B2 | 8/2009 | Townsend et al. |
| 7,618,464 B2 | 11/2009 | Christensen |
| 7,655,050 B2 | 2/2010 | Palmer |
| 7,686,848 B2 | 3/2010 | Christensen |
| 7,727,285 B2 | 6/2010 | Christensen |
| 7,740,602 B2 | 6/2010 | Christensen |
| 7,771,488 B2 | 8/2010 | Asgeirsson et al. |
| 7,794,506 B2 | 9/2010 | Christensen |
| 7,824,446 B2 | 11/2010 | Christensen et al. |
| 7,846,213 B2 | 12/2010 | Lecomte et al. |
| 7,951,101 B2 | 5/2011 | Pusch |
| 7,955,399 B2 | 6/2011 | Townsend et al. |
| 8,007,544 B2 | 8/2011 | Jonsson et al. |
| 8,034,121 B2 | 10/2011 | Christensen |
| 8,070,828 B2 | 12/2011 | Shannon |
| 8,092,550 B2 | 1/2012 | McCarvill et al. |
| 8,202,325 B2 | 6/2012 | Albrecht-Laatsch et al. |
| 8,246,695 B2 | 8/2012 | Mosler |
| 8,317,877 B2 | 11/2012 | Doddroe et al. |
| 8,474,329 B2 | 7/2013 | Schulze et al. |
| 8,500,825 B2 | 8/2013 | Christensen et al. |
| 8,771,370 B2 | 7/2014 | Albrecht-Laatsch et al. |
| 8,771,372 B1 | 7/2014 | Rubie |
| 8,900,326 B2 | 12/2014 | Doddroe et al. |
| 8,945,238 B2 | 2/2015 | Mosler et al. |
| 9,161,846 B2 | 10/2015 | Mosler |
| 9,351,853 B2 | 5/2016 | Doddroe et al. |
| 2002/0013628 A1 | 1/2002 | Harris |
| 2002/0040249 A1 | 4/2002 | Phillips |
| 2002/0133237 A1 | 9/2002 | Christesen |
| 2002/0188355 A1 | 12/2002 | Chen |
| 2003/0109638 A1 | 6/2003 | Briggs et al. |
| 2004/0225375 A1 | 11/2004 | Chen |
| 2004/0236435 A1 | 11/2004 | Chen |
| 2005/0033450 A1 | 2/2005 | Christensen |
| 2005/0033451 A1 | 2/2005 | Aigner et al. |
| 2005/0038525 A1 | 2/2005 | Doddroe |
| 2005/0071017 A1 | 3/2005 | Lecomte et al. |
| 2005/0187640 A1 | 8/2005 | Christensen |
| 2005/0203640 A1 | 9/2005 | Christensen |
| 2005/0216098 A1 | 9/2005 | Christensen |
| 2006/0069450 A1 | 3/2006 | McCarvil et al. |
| 2006/0167563 A1 | 7/2006 | Johnson et al. |
| 2006/0212131 A1 | 9/2006 | Curtis |
| 2006/0224246 A1 | 10/2006 | Clausen |
| 2006/0241782 A1 | 10/2006 | Curtis |
| 2006/0241783 A1 | 10/2006 | Christensen |
| 2007/0100466 A1 | 5/2007 | Allert |
| 2008/0033578 A1 | 2/2008 | Christensen |
| 2008/0167730 A1 | 7/2008 | Pusch |
| 2008/0188951 A1 | 8/2008 | Christensen et al. |
| 2008/0228288 A1 | 9/2008 | Nelson et al. |
| 2008/0312752 A1 | 12/2008 | Miller |
| 2009/0076626 A1 | 3/2009 | Ochoa |
| 2009/0105845 A1 | 4/2009 | Curtis |
| 2009/0157197 A1 | 6/2009 | Bonacini |
| 2009/0204229 A1 | 8/2009 | Mosler et al. |
| 2009/0204231 A1 | 8/2009 | Bonacini |
| 2010/0004757 A1 | 1/2010 | Clausen et al. |
| 2010/0042228 A1 | 2/2010 | Doddroe et al. |

(56) References Cited

U.S. PATENT DOCUMENTS

| | | | |
|---|---|---|---|
| 2011/0009982 A1 | 1/2011 | King et al. |
| 2011/0029097 A1 | 2/2011 | Ochoa |
| 2011/0197682 A1 | 8/2011 | Palmer |
| 2011/0199101 A1 | 8/2011 | Steele |
| 2011/0202144 A1 | 8/2011 | Palmer |
| 2011/0208322 A1 | 8/2011 | Rifkin et al. |
| 2011/0320012 A1 | 12/2011 | Christensen et al. |
| 2012/0046760 A1 | 2/2012 | Nissels et al. |
| 2012/0179274 A1 | 7/2012 | Christensen |
| 2012/0205206 A1 | 8/2012 | Chen et al. |
| 2012/0209406 A1 | 8/2012 | Chen et al. |
| 2012/0271434 A1 | 10/2012 | Friesen et al. |
| 2013/0030549 A1 | 1/2013 | Zahedi |
| 2013/0066439 A1 | 3/2013 | Zamora et al. |
| 2013/0173023 A1 | 7/2013 | Lecomte et al. |
| 2013/0289742 A1 | 10/2013 | Halldorsson et al. |
| 2014/0018938 A1 | 1/2014 | Bertels et al. |
| 2014/0046456 A1 | 2/2014 | Smith et al. |
| 2014/0156027 A1 | 6/2014 | Smith et al. |
| 2014/0243997 A1 | 8/2014 | Clausen et al. |
| 2014/0336782 A1 | 11/2014 | Mosler et al. |
| 2015/0134081 A1 | 5/2015 | Geiger et al. |
| 2015/0282953 A1 | 10/2015 | Smith et al. |
| 2015/0289996 A1 | 10/2015 | Smith |
| 2016/0038311 A1 | 2/2016 | Gonzalez et al. |
| 2016/0158030 A1 | 6/2016 | Doddroe et al. |

FOREIGN PATENT DOCUMENTS

| | | | |
|---|---|---|---|
| CN | 2075074 U | 9/1990 |
| CN | 2178511 U | 12/1993 |
| CN | 2614649 Y | 5/2004 |
| CN | 2614650 Y | 5/2004 |
| CN | 2614651 Y | 5/2004 |
| CN | 201524155 U | 7/2010 |
| CN | 101621973 A | 12/2011 |
| CN | 102665614 A | 3/2016 |
| DE | 20307200 U1 | 6/2003 |
| DE | 20307948 U1 | 7/2003 |
| DE | 20307949 U1 | 7/2003 |
| DE | 102014006571 B3 | 8/2015 |
| DE | 102014006687 A1 | 11/2015 |
| EP | 0401864 B1 | 11/1992 |
| EP | 1395209 B1 | 6/2010 |
| TW | 229414 | 11/1993 |
| TW | 339646 | 9/1998 |
| TW | 340371 | 9/1998 |
| TW | 353939 | 3/1999 |
| TW | 382260 | 2/2000 |
| TW | M253331 | 12/2004 |
| TW | M291283 | 6/2006 |
| TW | M336777 U | 7/2008 |
| TW | D124156 | 8/2008 |
| TW | D124157 | 8/2008 |
| TW | M377969 U | 4/2010 |
| TW | M409061 U | 8/2011 |
| TW | M438897 U | 10/2012 |
| TW | M438898 U | 10/2012 |
| TW | M450362 U | 4/2013 |
| TW | M467446 U | 12/2013 |
| TW | M484416 U | 8/2014 |
| WO | 93/24080 A1 | 12/1993 |
| WO | 2005027802 A1 | 3/2005 |
| WO | 2006099580 A2 | 9/2006 |
| WO | 2008070177 A1 | 6/2008 |
| WO | 2011133717 A1 | 10/2011 |
| WO | 2012005856 A1 | 1/2012 |
| WO | 2012009319 A2 | 1/2012 |
| WO | 2013101848 A1 | 7/2013 |
| WO | 2014008306 A1 | 1/2014 |
| WO | 2014147070 A1 | 9/2014 |
| WO | 2015169443 A1 | 11/2015 |

OTHER PUBLICATIONS

Moloney et al., "Parameters determining the strength and toughness of particulate filled epoxide resins," Journal of Materials Science, Feb. 1, 1987, pp. 381-393.

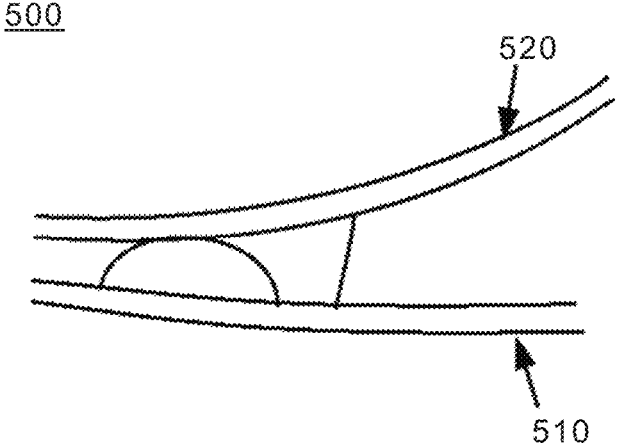
Fig. 5A
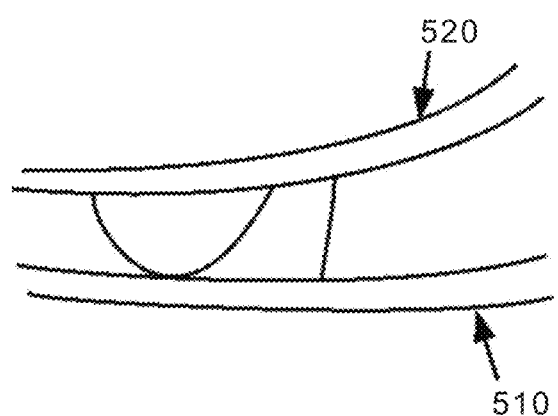
Fig. 5B
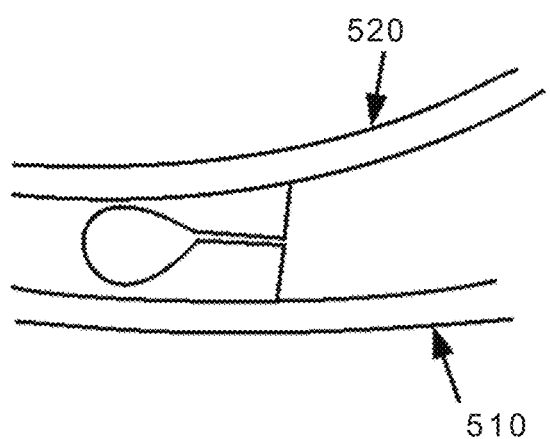
Fig. 5C
FIGs. 5A-5C

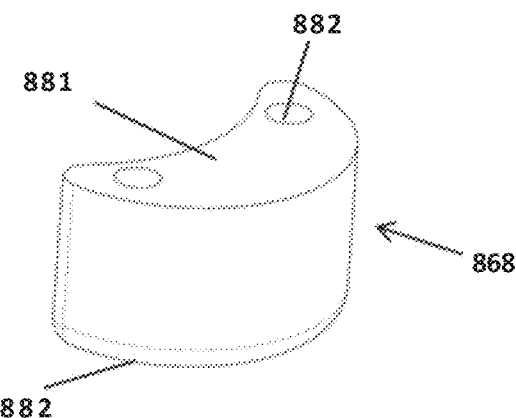
Figure 23A
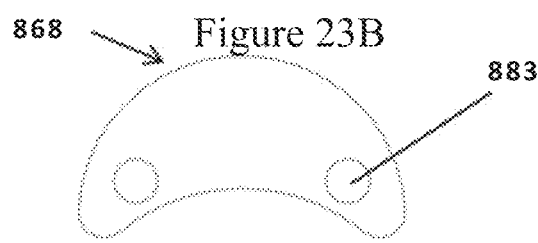
Figure 23B
Figure 23C
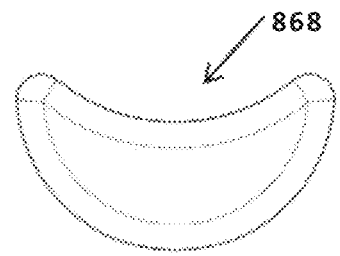

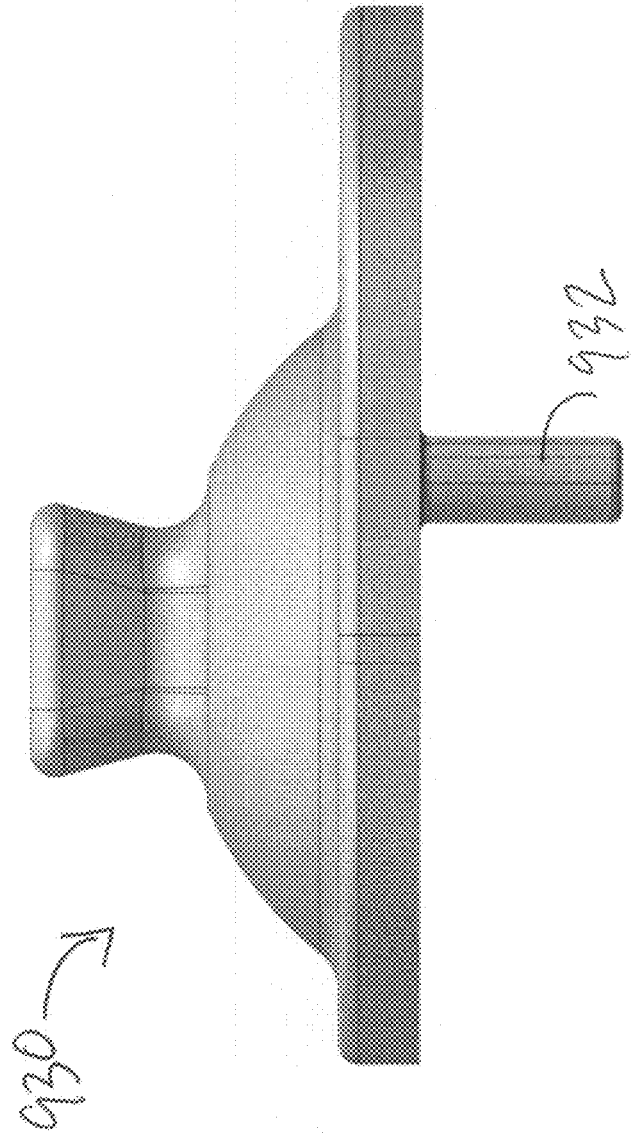

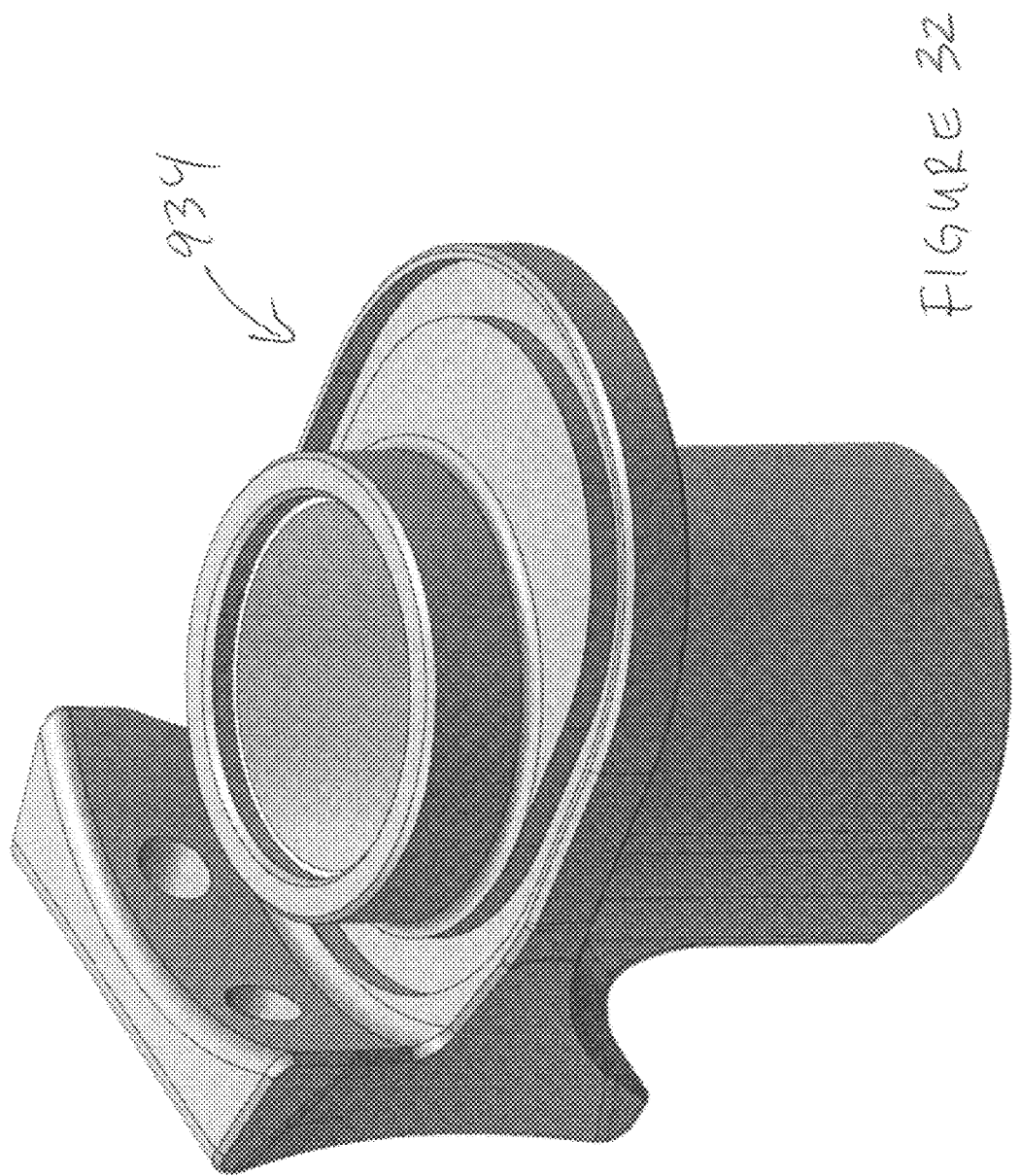

MOUNTING BRACKET FOR CONNECTING A PROSTHETIC LIMB TO A PROSTHETIC FOOT

CROSS-REFERENCES TO RELATED APPLICATIONS

The present application claims the benefit of U.S. Provisional Application Ser. No. 62/407,954, filed Oct. 13, 2016, U.S. Provisional Application Ser. No. 62/451,870, filed Jan. 30, 2017, and U.S. Provisional Application Ser. No. 62/539,743, filed Aug. 1, 2017; and is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012; and this application is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation in part of U.S. patent application Ser. No. 14/976,129, filed Dec. 21, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation-in-part of U.S. patent application Ser. No. 14/731,771, filed Jun. 5, 2015, which is a continuation of U.S. patent application Ser. No. 13/642,501, filed on Nov. 27, 2012, now U.S. Pat. No. 9,078,773, which is a 371 national phase application of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173 and incorporates the disclosure of all such applications by reference, and this application incorporates the disclosure of all such applications by reference.

FIELD OF THE INVENTION

This invention pertains to prosthetic devices. More particularly, the invention pertains to a prosthetic foot and mounting bracket for a prosthetic foot that, when utilized by an amputee, better replicates the action of a real foot and reduces the risk of injury to the amputee.

BACKGROUND OF THE INVENTION

Prosthetic feet are well known in the art. In use, such prosthetic feet typically do not replicate the action of a real foot and can generate "kickback" or "kickforward" reactions that increase the risk of injury to an amputee utilizing the foot. Kickback is motion created by the prosthetic foot in a backward direction during the walking cycle. Kickforward is motion created by the prosthetic foot in a forward direction during the walking cycle. Either motion may create instability for the user if expanding or restricting the intended motion. Further, many prior art prosthetic feet generate vibrations that can travel through a user's leg and cause discomfort.

For an amputee, losing bipedality may produce an involuntary anterior lean or shift, forcing a constant imbalance or rebalance of posture. The amputee no longer possesses voluntary muscle control on his involved side due to the severance of the primary flexor and extensor muscles. The primary anterior muscle responsible for dorsiflexion (sagittal plane motion) is the anterior tibialis. Dorsiflexion is the voluntary ankle motion that elevates the foot upwards, or towards the midline of the body. The primary posterior muscle responsible for plantarflexion is the gastro-soleus complex. It is a combination of two muscles working in conjunction: the gastrocnemius and the soleus. Plantarflexion is the voluntary ankle motion that depresses the foot downwards, or away from the midline of the body. Therefore, it is desirable to have a prosthetic foot configured to promote increased muscle activity and promote increased stability for amputees, and it is desirable to provide an improved prosthetic foot which would better replicate the action of a true foot. Furthermore, it is desirable to provide an improved prosthetic foot which minimizes or eliminates "kickback" forces when the foot is utilized to walk over a door jamb or other raised profile object on a floor or on the ground, as well as reduce vibrations.

In use, such prosthetic feet are typically mounted to either an above knee amputation or a below knee amputation and are designed to mimic the natural gait of a user. Depending on the type of amputation, different types of mounting systems may be utilized. For example, if the amputation is above the knee, various suspension systems may be utilized in conjunction with the prosthetic foot to enhance the feel, fit, and function. An above the knee amputation allows for multiple options as there is significant space between the residual limb and the prosthetic foot. With a below the knee amputation, depending on the location, there may be less space between the user's residual limb and the prosthetic foot thereby allowing for different attachment configurations for the prosthetic foot.

SUMMARY OF THE INVENTION

An exemplary mounting bracket for a prosthetic foot may comprise an upper member, a lower member, and a compression torsion joint connecting the upper member to the lower member. The upper member may be configured for attachment to a user's residual limb. The lower member may be configured to attach to the prosthetic foot.

Furthermore, in another embodiment, a prosthetic foot may comprise a resilient bottom member having a first bottom end and a second bottom end, a resilient top member having a first top end and a second top end, wherein the first top end is connected to the first bottom end of the resilient bottom member, and wherein the resilient top member is connected to a mounting bracket and positioned over the resilient bottom member and directed towards the back of the prosthetic foot, and a toe pad. The toe pad can comprise at least one spacer coupled to, and creating space between, the first bottom end of the bottom member and the first top end of the top member, and an adhesive bonding the first bottom end of the bottom member and the first top end of the top member, wherein the adhesive is commingled with the at least one spacer between the first bottom end and the first top end.

BRIEF DESCRIPTION OF THE DRAWINGS

These and other features, aspects and advantages of the present invention will become better understood with reference to the following description, appending claims, and accompanying drawings where:

FIG. 5A-5C are side views illustrating various embodiments of a damper bar configuration;

FIG. 23A is a perspective view representatively illustrating a bumper of the mounting bracket in accordance with exemplary embodiments of the present technology;

FIG. 23B is a top view representatively illustrating the bumper of the mounting bracket in accordance with exemplary embodiments of the present technology;

FIG. 23C is a top view representatively illustrating the bumper of the mounting bracket in accordance with exemplary embodiments of the present technology;

FIG. 31 is a side view representatively illustrating an additional embodiment of the upper member of the mounting bracket in accordance with exemplary embodiments of the present technology; and FIG. 32 is a perspective view representatively illustrating an additional embodiment of a lower member of the mounting bracket in accordance with exemplary embodiments of the present technology.

Figure 1A:
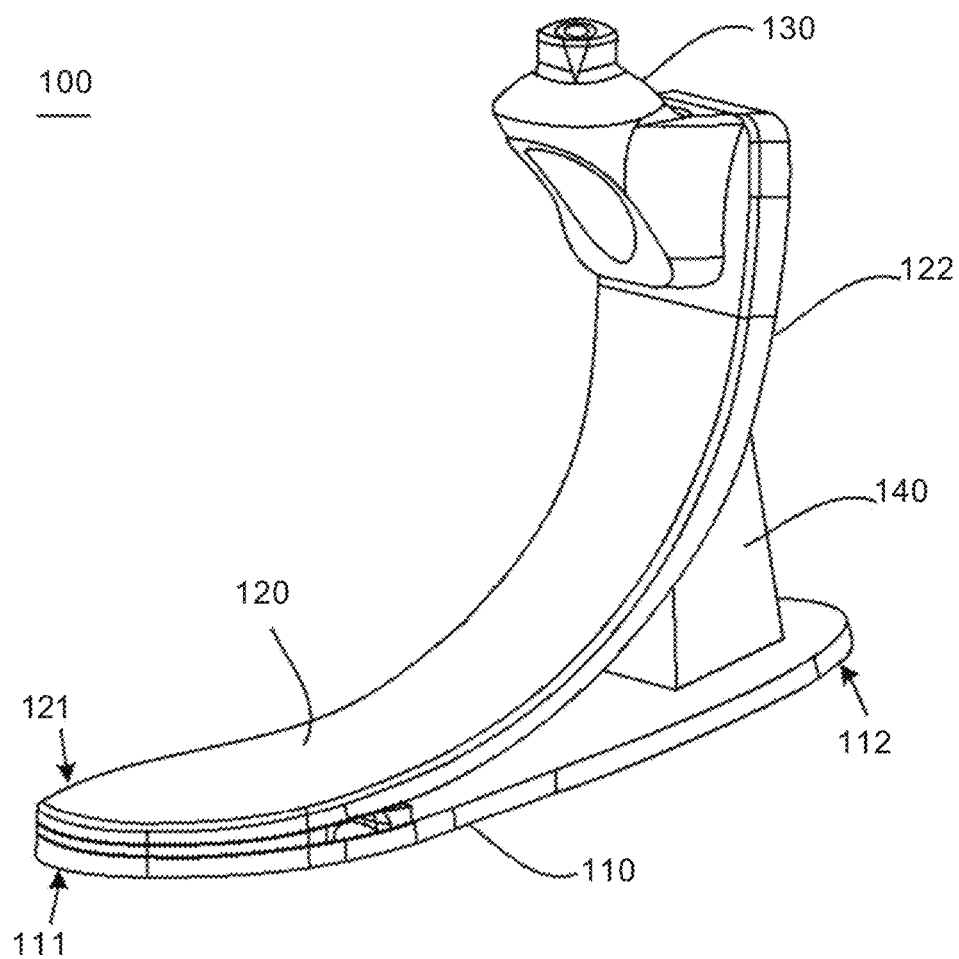
FIGS. 1A and 1B are perspective views illustrating a prosthetic foot constructed in accordance with various embodiments.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may be used with a prosthetic foot for various amputation types (above knee, below knee, etc.). In addition, the present technology may be practiced in conjunction with any number of materials and methods of manufacture and the system described is merely one exemplary application for the technology.

While exemplary embodiments are described herein in sufficient detail to enable those skilled in the art to practice the invention, it should be understood that other embodiments may be realized and that logical structural, material, and mechanical changes may be made without departing from the spirit and scope of the invention. Thus, the following descriptions are not intended as a limitation on the use or applicability of the invention, but instead, are provided merely to enable a full and complete description of exemplary embodiments.

Briefly, in accordance with exemplary embodiments, a prosthetic foot has improvements over a prior art prosthetic foot in that a more natural motion and response of the foot occurs during movement. In particular, the movement of the exemplary prosthetic foot replicates the natural flex of a foot and supplies continuous energy to a person when striding from heel to toe.

Briefly, in accordance with exemplary embodiments, a mounting bracket for a prosthetic foot is illustrated, which comprises a more natural motion and response during movement. In particular, the movement of the mounting bracket may replicate the natural movement of a foot, provide vertical shock absorption and allow for torsional rotation.

A typical prosthetic foot stores energy during the gait cycle and transfers the return potential energy in order to "put a spring in your step." The roll through of a prosthetic foot is defined in the gait cycle as the process from the heel-strike phase to the mid-stance phase to the toe-off phase. The heel-strike phase begins when the heel of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe. This is just prior to the swing phase, which constitutes the other half of the gait cycle.

As the user moves through the stance phase portion of the gait cycle the tibia portion of the leg, or that section of the leg defined below the knee, rotates through in relation to the ground. If the mid-stance phase is defined as the lower leg at 90 degrees to the ground, then looking at the side view of an individual, the angle of the lower leg at the heel-strike phase may occur at approximately 65 degrees and the angle of the lower leg at the toe-off phase may occur at approximately 110 degrees. The rotation of the lower leg on the theoretical ankle is notated as tibial progression or lower leg progression during the stance phase. The mounting bracket provides vertical shock absorption though the gait cycle and while standing and further allows for torsional rotation.

Figure 1B:
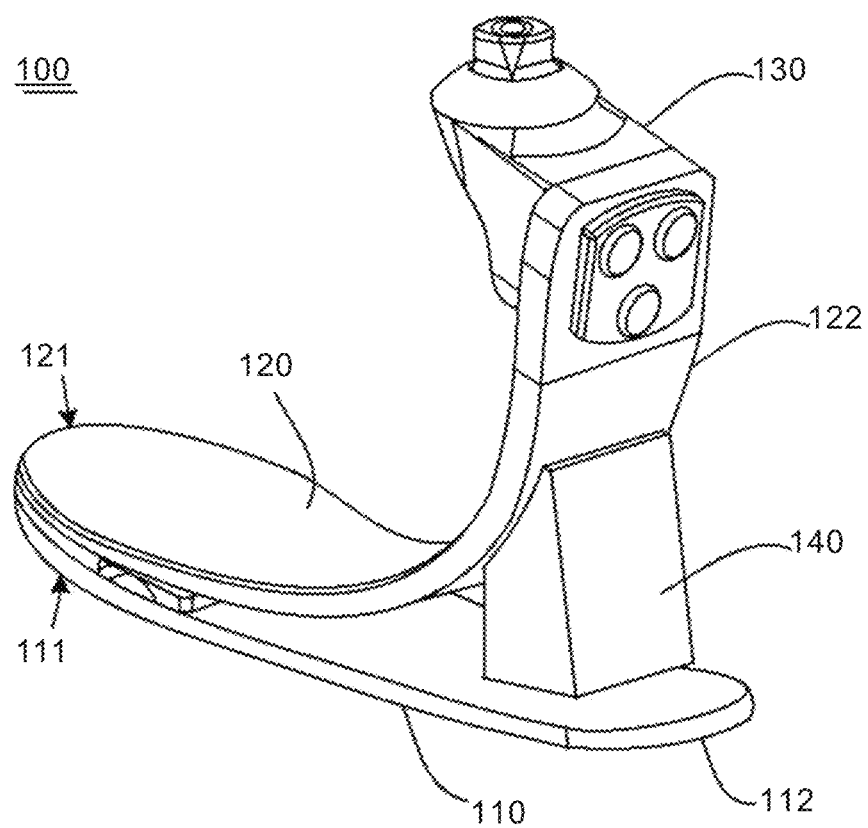

In accordance with various embodiments and with reference to FIGS. 1A and 1B, a prosthetic foot 100 comprises a resilient bottom member 110, a resilient top member 120, a connection point 130 attached to the top member 120 and configured for attachment to a user, and a bumper member 140. The resilient bottom member 110 may have an anterior bottom end 111 and a posterior bottom end 112. The resilient top member 120 may have an anterior top end 121 and a posterior top end 122. Further, the anterior top end 121 of the resilient top member 120 can be connected to the anterior bottom end 111 of the resilient bottom member 110, while the resilient top member 120 can be positioned over the resilient bottom member 120 and directed towards the posterior of the prosthetic foot 100.

Further, in various embodiments, prosthetic foot 100 also comprises an elastomeric bumper member 140 having a tapered surface configured to contact the resilient bottom member 110 and attached to an underside of the posterior top end 122 of the resilient top member 120. The bumper member 140 can be vertically oriented with respect to the prosthetic foot 100. The bumper member 140 can act as a heel shock for absorbing force on the downward strike during the user's stride.

In various embodiments, the bumper member 140 can be made from an elastomeric material. In one embodiment, the elastomeric material has about 80% or greater energy return. In another embodiment, the elastomeric material has about 90% or greater energy return. The bumper member 140 can be designed to behave similar to a non-linear spring, thereby allowing larger deflection of the posterior toe and 122 during the heel strike. The progressive "spring rate" may lead to a soft heel strike but does not deflect too far as the bumper member 140 compresses. One benefit of the bumper 140 is being relatively lightweight in comparison to a prosthetic foot with coiled springs.

Figure 2:
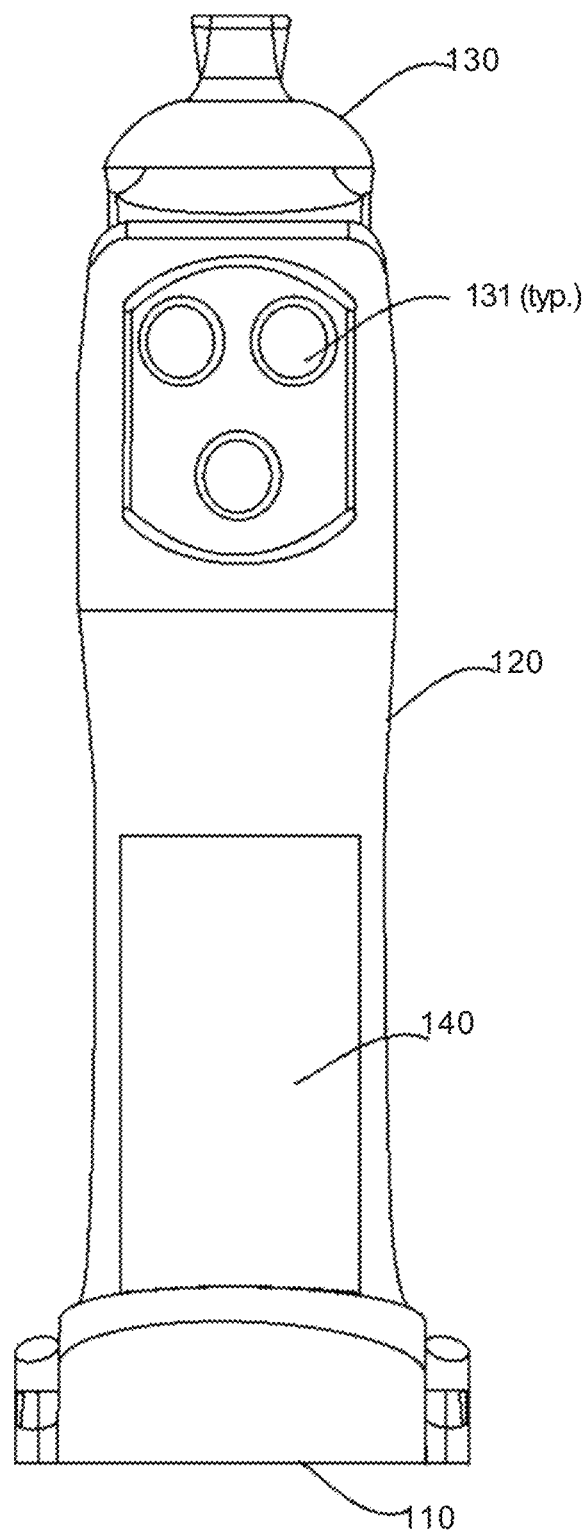
FIG. 2 is a rear view further illustrating the prosthetic foot of FIGS. 1A and 1B.

The bumper member 140 can be located posterior to vertical axis of the connection point 130. The bumper member 140 can be attached to the underside of the top member 120 in various manners. For example and with reference to FIG. 2, the bumper member 140 can be fixedly attached using adhesive or fasteners, such as screws. In another example, the bumper member 140 may be detachable using fasteners for replacement purposes. Moreover, in other embodiments, the bumper member 140 can be attached to various locations on the underside of the top member 120 or topside of the bottom member 110. In various embodiments, the prosthetic foot 100 in a static mode has a gap between the bumper member 140 and the bottom member 110. For example, a gap of about 1/10 inch may be present between the bumper member 140 and the bottom member 110. In other various methods, the bumper member 140 can be in contact with both the top member 120 and the bottom member 110 when the prosthetic foot 100 is in a static position. The lack of a gap results in the bumper member 140 being continuously compressed during the gait cycle, though the bumper member 140 is a compression member and not a tension member since the bumper member 140 is only attached to either the top member 120 or the bottom member 110. The bumper member 140 not being attached to the other of the top member 120 or the bottom member 110 provides flexibility during the gait cycle of the prosthetic foot 100 to more closely mimic a natural foot/ankle system. Connecting the bumper member 140 to both the resilient top and bottom members 120, 110 creates almost a triangle structure, which is very stiff.

The bumper member 140 can be in many shapes. In various embodiments, the detached portion of the bumper member 140 may have a conical, rectangular, or pyramid shape. The tapered surface of the bumper member 140 can terminate in an apex or hemispherical shape, and the apex can be configured to contact the bottom member 110 in response to deflection of the prosthetic foot 100. Moreover, in various embodiments, the bumper member 140 can terminate in multiple points. The tapered bumper member 140 facilitates a damping of vibration and sound generated during heel strike or release. Furthermore, in various embodiments the extruding portion of the bumper member 140 may be any shape that is non-flat surface. Further, a non-flat surface enhances lateral flexibility if the heel strike is not vertical.

The prosthetic foot 100 can be adjusted to accommodate a user in part by adjusting characteristics of the bumper member 140. For example, in various embodiments, the durometer of the bumper member 140 can be increased for users with more heel strike force, which may be caused by additional weight or dynamic activity. A heavier user may be better-suited using a bumper member with a large cross-sectional area compared to a lighter user using a bumper member with a small cross-sectional area.

Figure 3:
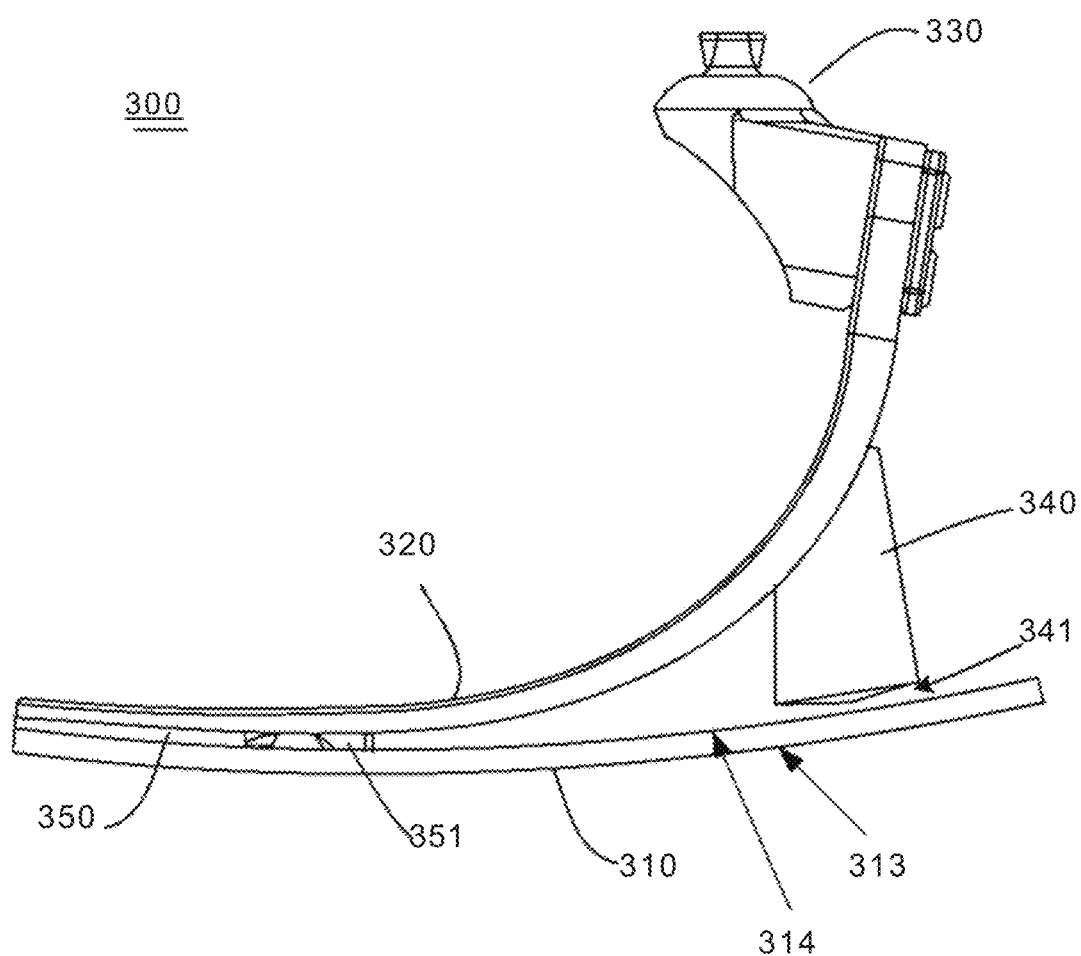
FIG. 3 is a side view further illustrating the prosthetic foot of FIGS. 1A and 1B.

In accordance with various embodiments and with reference to FIG. 3, a prosthetic foot 300 comprises a resilient bottom member 310, a resilient top member 320, a connection point 330 attached to the top member and configured for attachment to a user, and a toe pad 350 coupled to the top surface of the bottom member 310 at a first bottom end and coupled to the bottom surface of the top member 320 at a first top end. Also, in various embodiments, prosthetic foot 300 may further comprise a bumper member 340. In various embodiments, the toe pad 350 comprises at least one spacer and an adhesive bonding the top surface of the bottom member 310 and the bottom surface of the top member 320. For example, the anterior quarter of the bottom member 310 can be adhesively connected to the top member 320. In various embodiments, adhesive can be used to connect 23-27% of the top surface area of the bottom member 310 to the top member 320. Further, in various embodiments, adhesive can be used to connect approximately 1/3 of the top surface area of the bottom member 310 to the top member 320.

In various embodiments, the toe pad 350 has approximately constant thickness. In other various embodiments, the toe pad 350 can have a thickness that tapers towards the front edge of the prosthetic foot 300. In other words, the toe pad 350 closer to the heel can be thicker than the toe pad 350 closer to the toe. Further, the adhesive bonding of the toe pad 350 can produce distributed stresses. In accordance with various embodiments, the adhesive can have a higher modulus of elasticity in contrast to the elastomer of the toe pad. Though other modulus values are contemplated, and various moduli may be used as well, a stiffer adhesive is preferred compared to a flexible adhesive.

The spacer of the toe pad 350 creates a space between the top surface of the bottom member 310 and the bottom surface of the top member 320. The adhesive can be commingled with the spacer between the top surface of the bottom member 310 and the toe pad 350 and also between the bottom surface of the top member 320 and the toe pad 350. In various embodiments, the space created by the spacer can be non-compressed space for the placement of the adhesive. In other words, the spacer can create a void between the top member 320 and the bottom member 310 and the void can be filled with the adhesive for bonding. The inclusion of the toe pad 350 may reduce the stress applied to the adhesive bond during the gait cycle. In various embodiments, the spacer can be elastomeric stand-offs, such as dots, ribs, or other patterns to create the desired spacing. Moreover, in various embodiments, the spacer is a single piece of connected stand-offs. The single piece spacer facilitates easier alignment during the manufacturing process and can provide a more uniform stand-off pattern compared to multiple stand-off spacers.

The toe pad 350 can also comprise an adhesive composite with spacers. In various embodiments of the prosthetic foot 300, the spacer is an aggregate material combined with the adhesive to form the adhesive composite. In various embodiments, the adhesive composite includes adhesive and microspheres. The microspheres can create the spacing between the top and bottom members 320, 310.

Figure 4A:
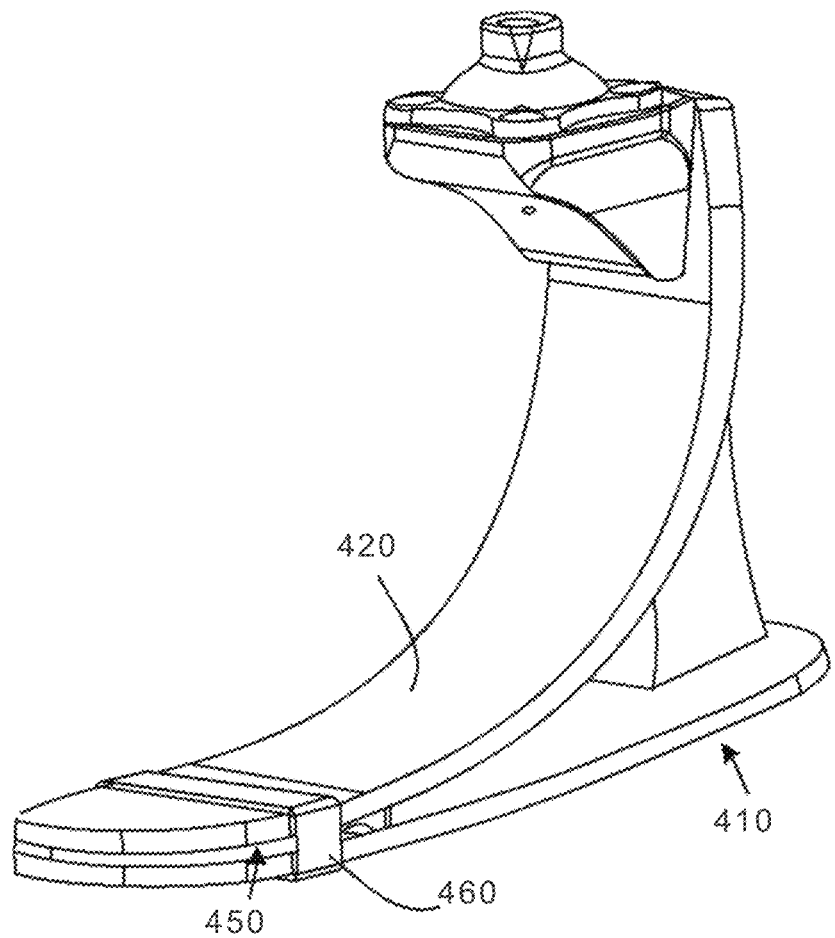
FIGS. 4A and 4B are perspective views illustrating a prosthetic foot comprising a toe wrap.
Figure 4B:
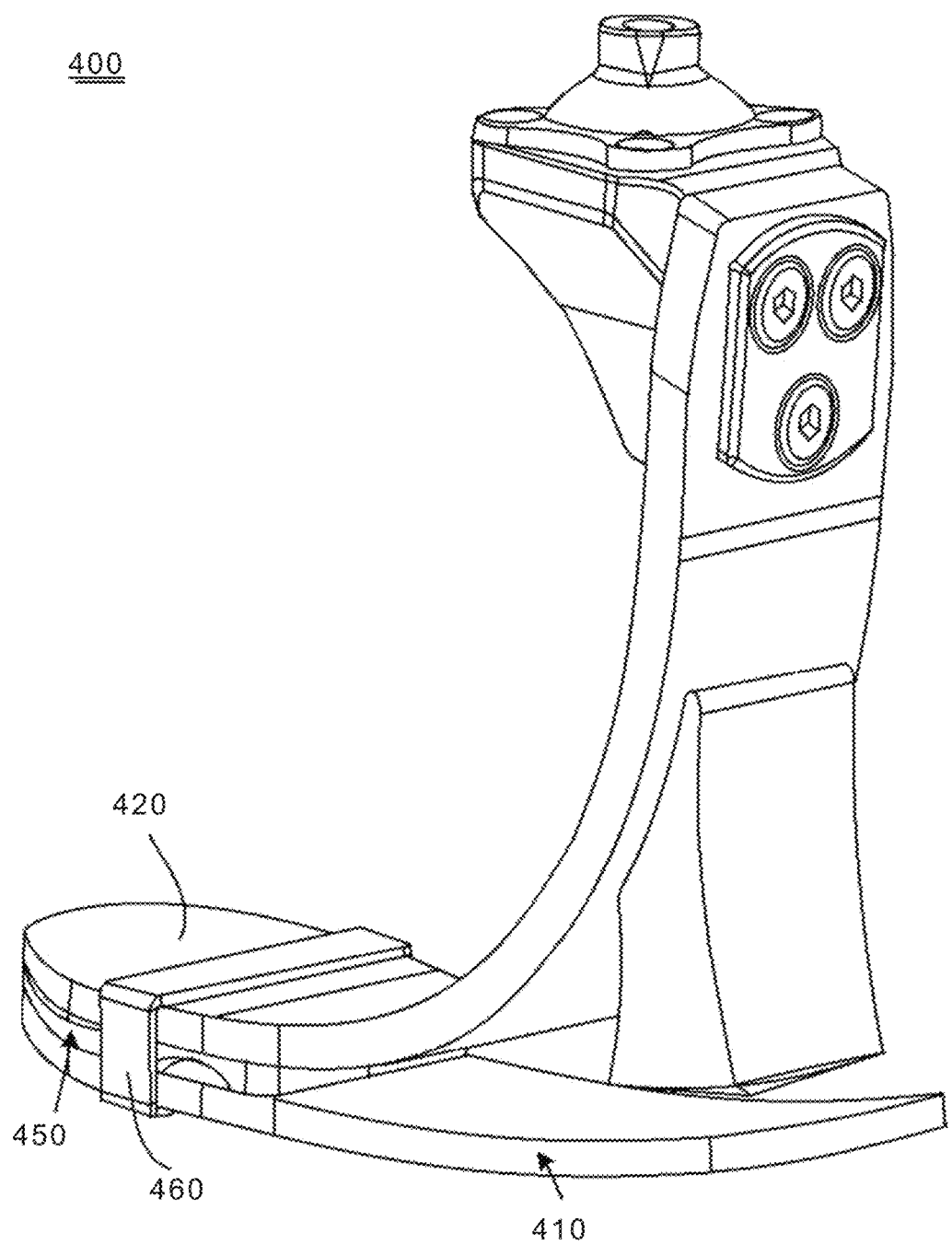

Additionally, in various embodiments and with reference to FIGS. 4A and 4B, a prosthetic foot 400 can comprise a bottom member 410, a top member 420, a toe pad 450, and a toe wrap 460 bonded around the top and bottom of the bonded bottom and top members 410, 420. The toe wrap 460 can be made out of a fiber material. The toe wrap material can also be a fiber weave with an elastomeric material. For example, the toe wrap can be a Kevlar or nylon material belt that is approximately less than a 1/10$^{th}$ of an inch in thickness. The toe wrap 460 can be configured to provide a secondary hold in case the adhesive bond of the toe pad 450 between the top and bottom members breaks. Also, the toe wrap 460 can strengthen the attachment between the bottom and top members 410, 420 during tension.

Moreover, in various embodiments and with renewed reference to FIG. 3, the prosthetic foot 300 can further comprise a damper bar 351 configured to attach to an underside of the resilient top member 320 and contact the resilient bottom member 310. The damper bar 351 can be configured to arrest the upward motion of bottom member 310 after toe off and also arrest the rotational energy during the gait cycle. The arrested motion creates a slower velocity and less motion at the point of contact of the damper bar 351. Without the damper bar, the bottom member 310 may slap against the bumper member 340 during the stride, resulting in vibration traveling up the leg of the user.

In various embodiments, the damper bar 351 can be located near the posterior edge of the toe pad 350. As an example, the damper bar 351 can be spaced 1/2 inch away from the posterior edge of the toe pad 350. In another example, the damper bar 351 can be located in the anterior portion of the bottom member 310. Further, the damper bar 351 can be approximately a ½ inch long, with the length measured from anterior to posterior of the bottom member 310. In various embodiments, the width of the damper bar 351 can be as wide as the attached top member 320. However, the damper bar 351 may also be less than the full width of the attached top member 320. Furthermore, in various embodiments, the contacting surface of the damper bar 351 can be flat. In alternative embodiments, the contacting surface of the damper bar 351 can be tapered to an apex. The contacting surface can be configured to reduce vibration and sounds caused from the contact of the non-connected bottom member 310 with the damper bar 351 during the gait cycle. Furthermore, in various embodiments, the contacting surface of the damper bar 351 can be various shapes other than flat, such as a preloaded taper.

In various embodiments, the damper bar 351 is connected to the toe pad 350, or is formed as part of the toe pad 350. One advantage of having the toe pad 350 and damper bar 351 as a single piece is for easier alignment during manufacturing of the prosthetic foot 300.

The damper bar 351 can be minimally load-bearing, whereas the bumper member 340 can be the primary load-bearing component. In various embodiments, the bumper member 340 can be located about four to five times farther back from the fulcrum point of the toe pad 350 in comparison to the damper bar 351. Furthermore, in various embodiments and with reference to FIGS. 5A-5C, a damper bar can be attached to the prosthetic foot in various configurations. For example, FIG. 5A illustrates a damper bar 551 attached to a top member 520, whereas FIG. 5B illustrates a damper bar 551 attached to a bottom member 510. In another example, FIG. 5C illustrates a damper bar 551 attached to both the bottom member 510 and the top member 520, where the damper bar 551 is divided such that the top and bottom member may separate and still arrest motion of the prosthetic foot.

Moreover and with renewed reference to FIGS. 1A and 1B, the top member 120, bottom member 110, and bumper member 140 transfer energy between themselves in a natural, true foot manner. The loading response during the heel strike phase compresses bumper member 140 and top member 120, which in turn passes energy into, and causes a deflection of, a rear portion of bottom member 110. Energy is transferred towards the front of prosthetic foot 100 during the mid-stance phase. Furthermore, an upward deflection of at least one of bottom member 110 and top member 120 stores energy during the transition from the mid-stance phase to the toe-off phase of the gait cycle. In an exemplary embodiment, about 90% or more of the heel strike loading energy is stored and transferred to top member 120 for assisting the toe-off phase. In another exemplary embodiment, about 95% or more of the heel strike loading energy is stored and transferred to top member 120 for assisting the toe-off phase. In yet another exemplary embodiment, about 98% or more of the heel strike loading energy is stored and transferred to top member 120 for assisting the toe-off phase. Prosthetic foot 100 may be designed to release the stored energy during the toe-off phase and assist in propelling the user in a forward direction.

In an exemplary embodiment and with renewed reference to FIG. 3, resilient bottom member 310 includes a bottom surface 313 and an upper surface 314. Resilient bumper member 340 includes a contact surface 341. When prosthetic foot 300 is compressed, resilient top member 320 and bumper member 340 are compressed and displaced downwardly toward resilient bottom member 310.

With respect to the walking motion, the prosthetic foot is configured to increase the surface-to-foot contact through the gait cycle. The increased surface contact allows for a smoother gait cycle, and increases stability in comparison to the typical prior art prosthetics. In exemplary embodiments, the underside of bottom member has different contours that provide increased surface contact for different types of uses.

Figure 6:
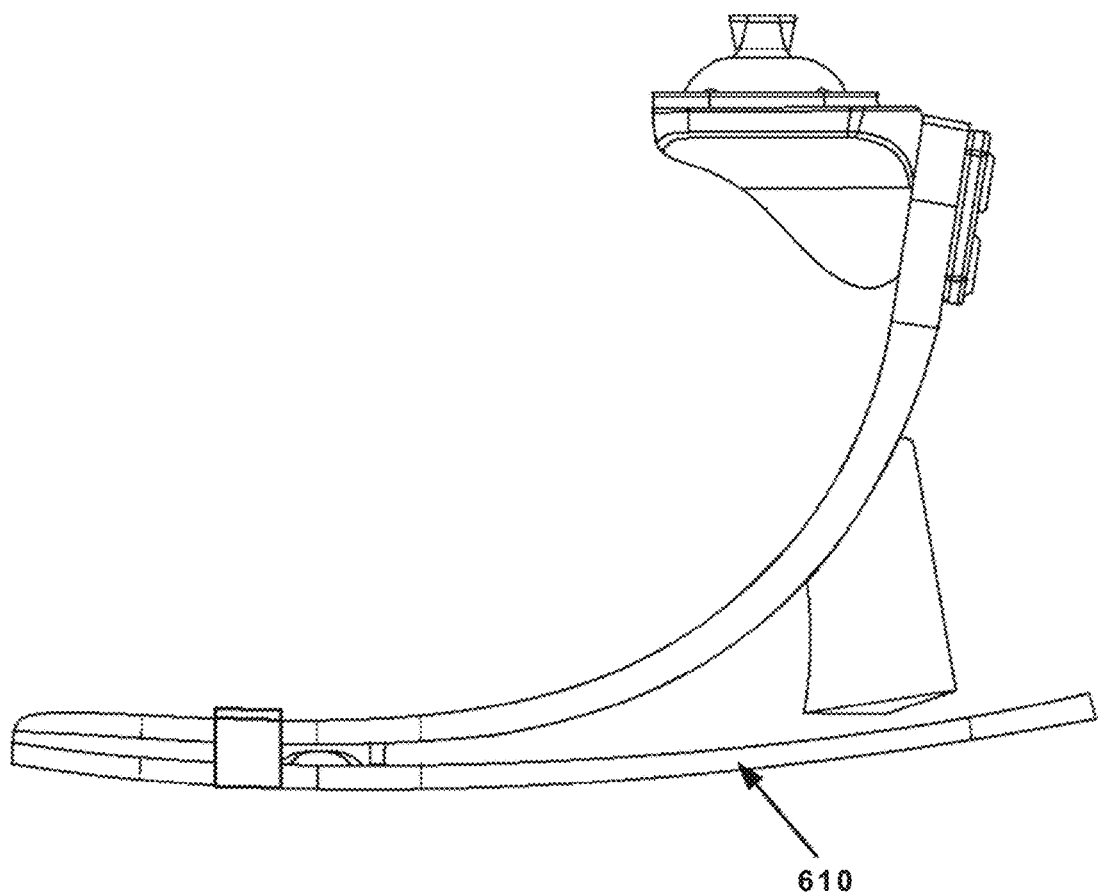
FIG. 6 is a side view illustrating an exemplary prosthetic foot for use by an above-knee amputee.

The bottom member of the prosthetic foot can have various shapes depending on desired use. The desired use may include prosthetic feet for above-knee amputees or prosthetic feet for below-knee amputees. In various embodiments and with reference to FIG. 6, a prosthetic foot 600 for above-knee amputees comprises a bottom member 610 having a curved bottom with no inflection point. In various embodiments, the bottom member 610 has a constant arc due to single radius forming the partial curve of the bottom member. In other various embodiments, the curve of the bottom member 610 can be designed as a spline of variable radii. The curve of bottom member 610 in above-knee prosthetic foot 600 facilitates keeping an artificial knee stable because the forces substantially restrict the knee from bending. The curved bottom member 610 enables a rocking motion even if the artificial knee is hyper-extended.

Figure 7:
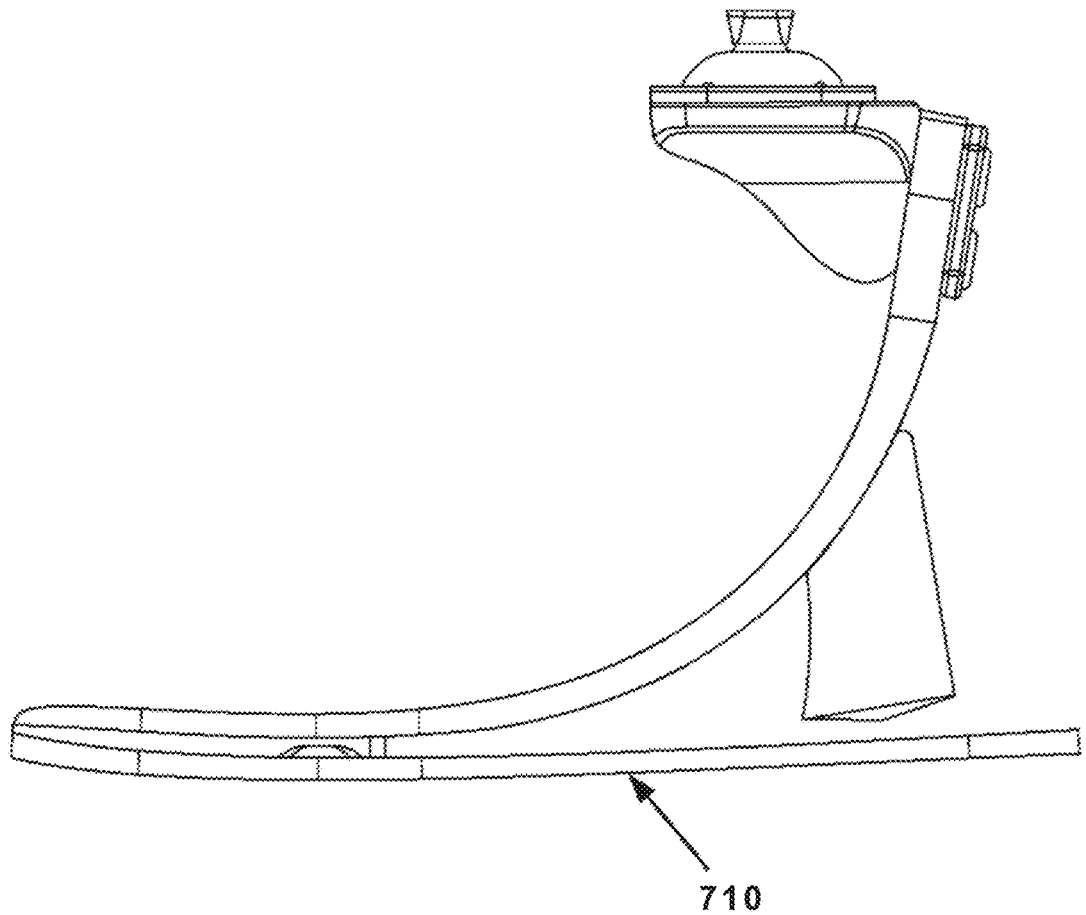
FIG. 7 is a side view illustrating an exemplary prosthetic foot for use by a below-knee amputee.

Similarly, in various embodiments and with reference to FIG. 7, a prosthetic foot 700 for below-knee amputees comprises a bottom member 710 having a partially curved portion in the anterior of the bottom member 710 and a substantially linear portion in the posterior portion of the bottom member 710. Similar to above-knee prosthetic foot 600, the anterior portion of bottom member 710 can have a constant arc due to single radius forming the partial curve. In various embodiments, the anterior portion of bottom member 710 can have a curve designed as a spline of variable radii. In accordance with various embodiments, the posterior portion of bottom member 710 can be substantially straight and tangent to the anterior portion such that bottom member 710 does not have an inflection point. A straight posterior portion and a curved anterior portion of bottom member 710 in below-knee prosthetic foot 700 facilitates rotation of the tibia progressing the natural rotation of the knee forward and preventing hyper-extension of the knee.

In accordance with an exemplary embodiment, resilient members 110, 120 are made of glass fiber composite. The glass fiber composite may be a glass reinforced unidirectional fiber composite. In one embodiment, the fiber composite material is made of multiple layers of unidirectional fibers and resin to produce a strong and flexible material. The fibers may be glass fibers or carbon fibers. Specifically, layers of fiber are impregnated with the resin, and a glass reinforcement layer can be positioned between at least two fiber weave layers. Typically, several layers of the unidirectional fibers or tape are layered together to achieve the desired strength and flexibility. Further, in various embodiments the layers of unidirectional fibers or tape can be oriented at various angles.

Figure 8:
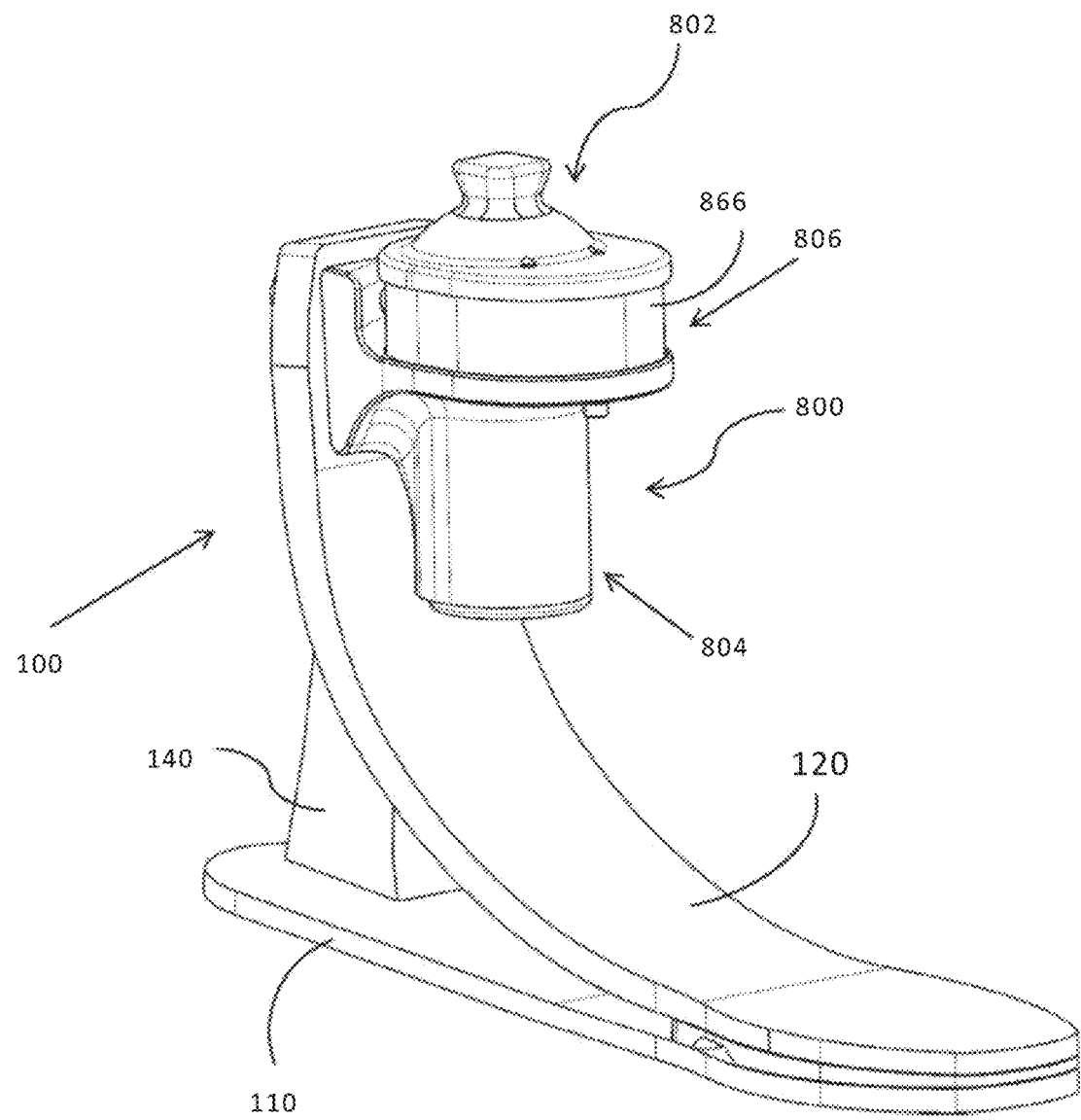
FIG. 8 is a perspective view representatively illustrating a mounting bracket on a prosthetic foot in accordance with exemplary embodiments of the present technology.
Figure 9:
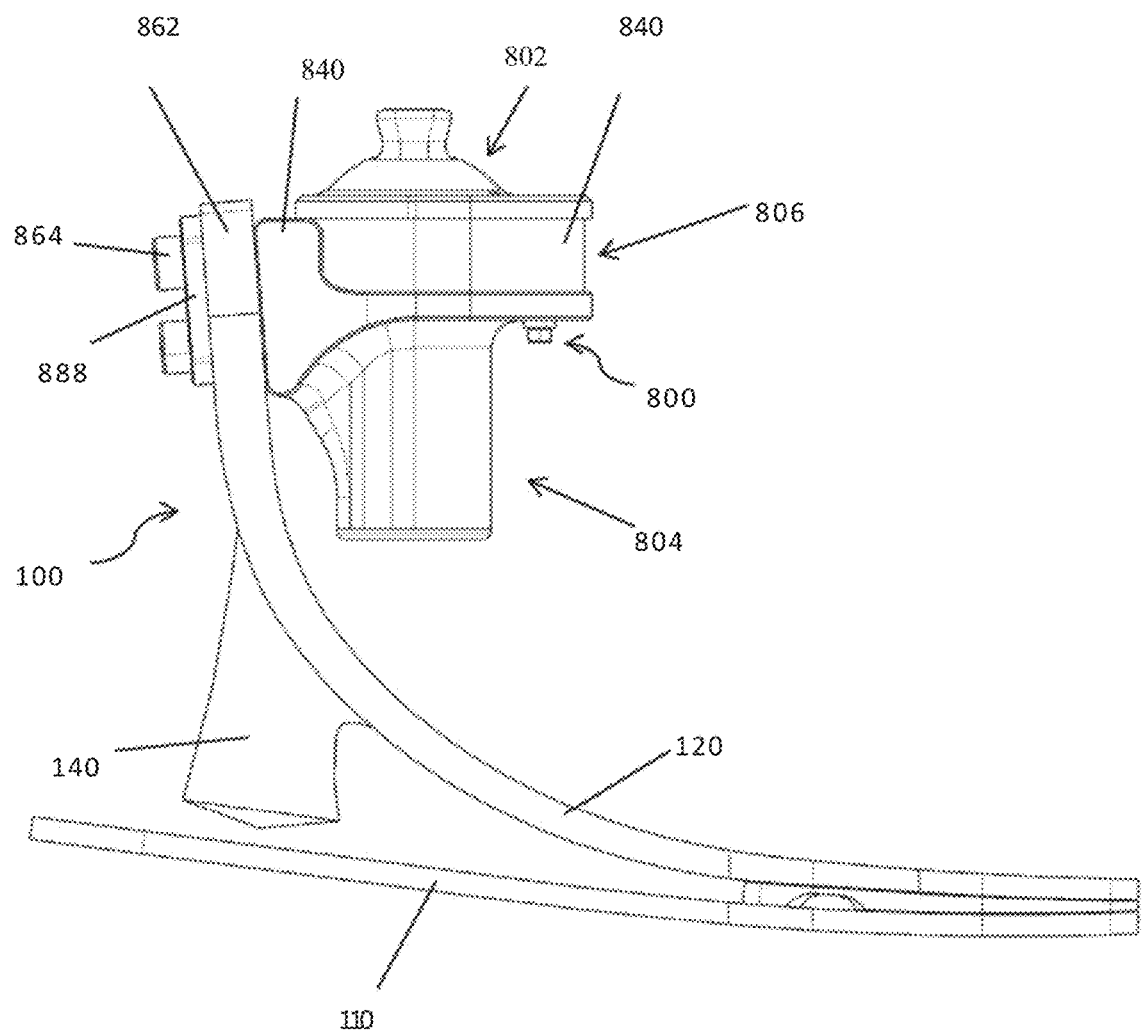
FIG. 9 is a side view representatively illustrating the mounting bracket on a prosthetic foot in accordance with exemplary embodiments of the present technology.
Figure 10:
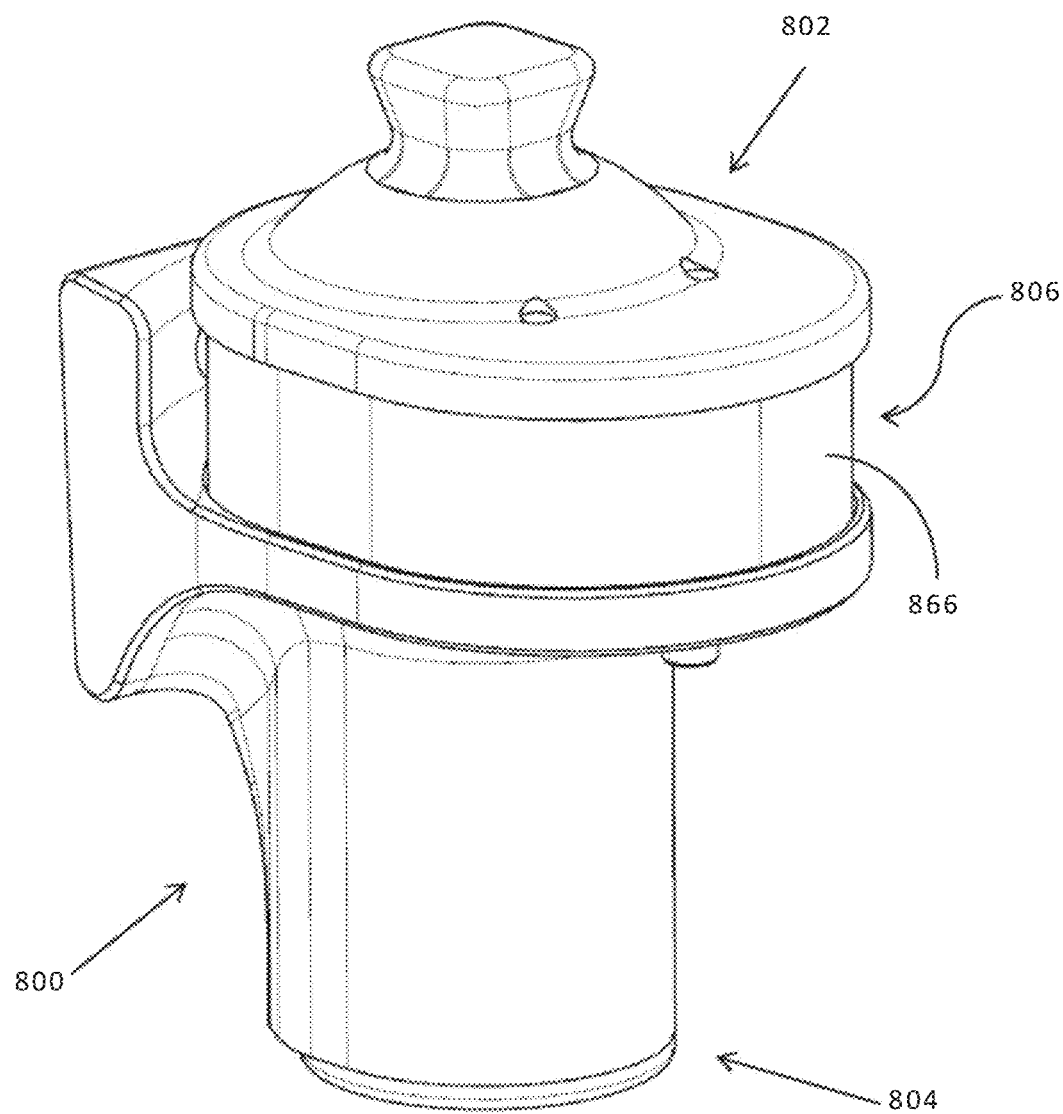
FIG. 10 is a perspective view representatively illustrating the mounting bracket in accordance with exemplary embodiments of the present technology.

In accordance with various embodiments and with reference to FIGS. 8-10, the connection point 130 may comprise a mounting bracket 800. The mounting bracket 800 may be attached to the top member 120 and configured for attachment to a user. In various embodiments, the mounting bracket 800 may comprise an upper member 802, a lower member 804, and a compression torsion joint 806. The upper member 802 may be configured for attachment to a user's residual limb. The lower member 804 may be configured to attach to a prosthetic foot. In one embodiment the lower member 804 is coupled to the prosthetic foot 100.

Figure 11A:
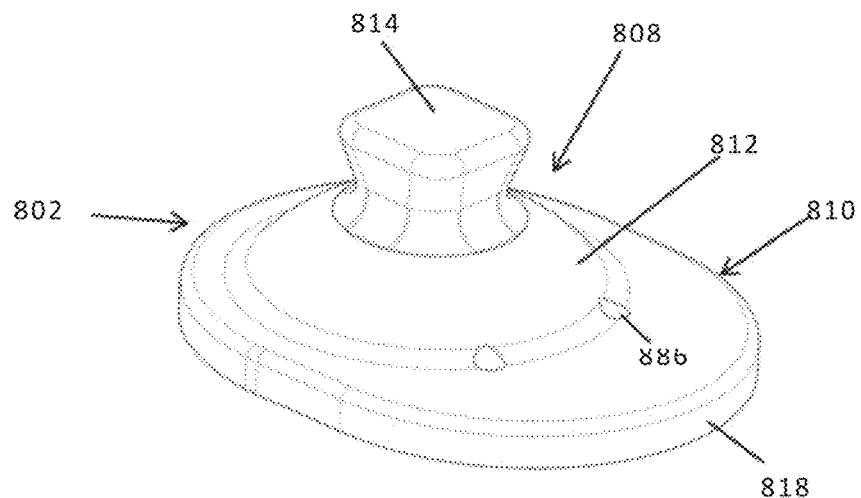
FIG. 11A is a perspective view representatively illustrating an upper member of the mounting bracket in accordance with exemplary embodiments of the present technology.
Figure 11B:
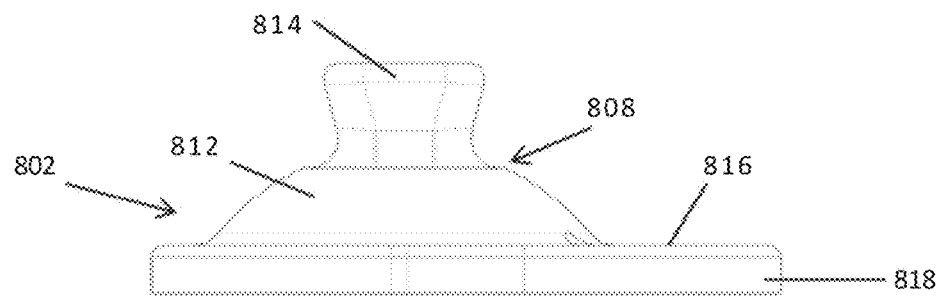
FIG. 11B is a side view representatively illustrating the upper member of the mounting bracket in accordance with exemplary embodiments of the present technology.
Figure 11C:
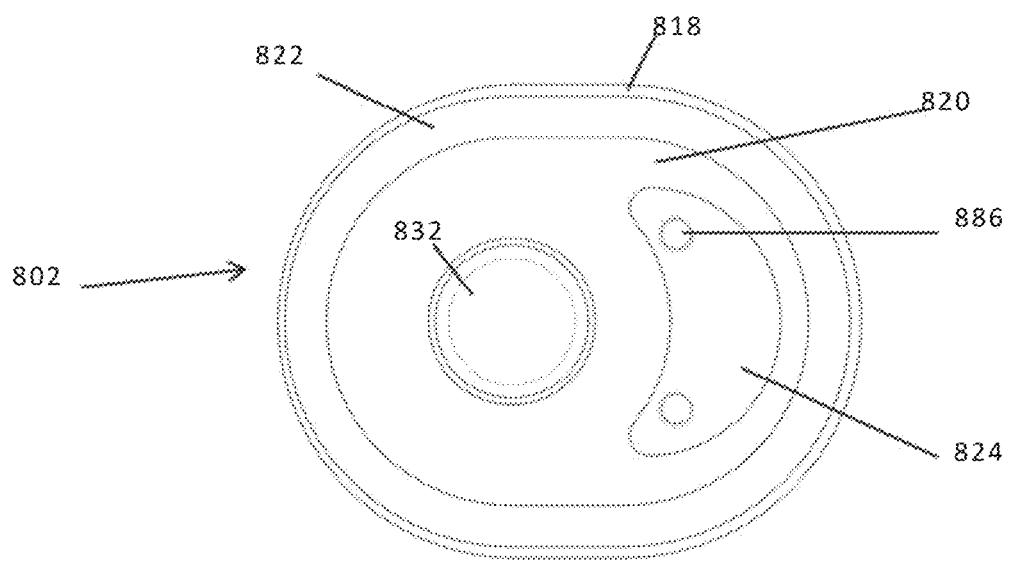
FIG. 11C is a bottom view representatively illustrating the upper member of the mounting bracket in accordance with exemplary embodiments of the present technology.

Referring now to FIG. 11A-C, in various embodiments, the upper member 802 may comprise mounting portion 808 and an upper flange 810. The mounting portion 808 may be configured to attach to a user's residual limb. The mounting portion 808 may comprise a spherical dome 812 and an attachment portion 814, which is a standard male pyramid adapter used in the prosthetic industry. The pyramid adapter may be coupled with a standard receiver used in the practice of prosthetics, for example, a Staats style attachment, which is commonly known in the prosthetic industry. The attachment portion 814 may use a standard receiver adapter, as understood by one of ordinary skill in the art. According to various embodiments the attachment portion 814 may facilitate attachment to the residual limb of the user. The attachment portion 814 may comprise a centerline that is aligned with the weight line of the user.

The spherical dome 812 may be located on an upper surface 816 of the upper flange 810. In various embodiments, the upper flange 810 may comprise a downwardly depending lip 818 around its perimeter and a lower surface 820 with a channel 822 contained therein. In various embodiments, the lower surface 820 of the upper flange 810 may comprise a recess 824. In one embodiment, the recess 824 may comprise a crescent-shaped recess 824.

In various embodiments, as shown in FIGS. 14B, 16, 19, 27A, and 27B the upper member 802 may also comprise a mating post 826. The mating post 826 may comprise a cylindrical collar 828 depending downwardly from the lower surface 820 of the upper flange 810. In various embodiments the mating post 826 may be removable. An upper portion 830 of the mating post 826 may be coupled to the upper member 802 within a recess 832 by any known method, such as screw fit, pressed, and the like. In one embodiment the mating post 826 may be coupled to the upper member 802 by a threaded connection. The mating post 826 may comprise threads (not shown) on the upper portion 830 of the cylindrical collar 828 that are received by threads (not shown) within the recess 832 in the upper member 802. The mating post 826 may further comprise at least one recess 834 on the perimeter of the cylindrical collar 828 that may receive O-rings (not shown). The O-rings serve to fill the clearance between the outer diameter of mating post 826 and the inner diameter of sleeve 902 to provide smooth, and silent action between relatively moving components. In one embodiment, the mating post 826 comprises at least one recess 836 on the perimeter of the cylindrical collar 828 that may receive grease or another lubricant during assembly.

Figure 12A:
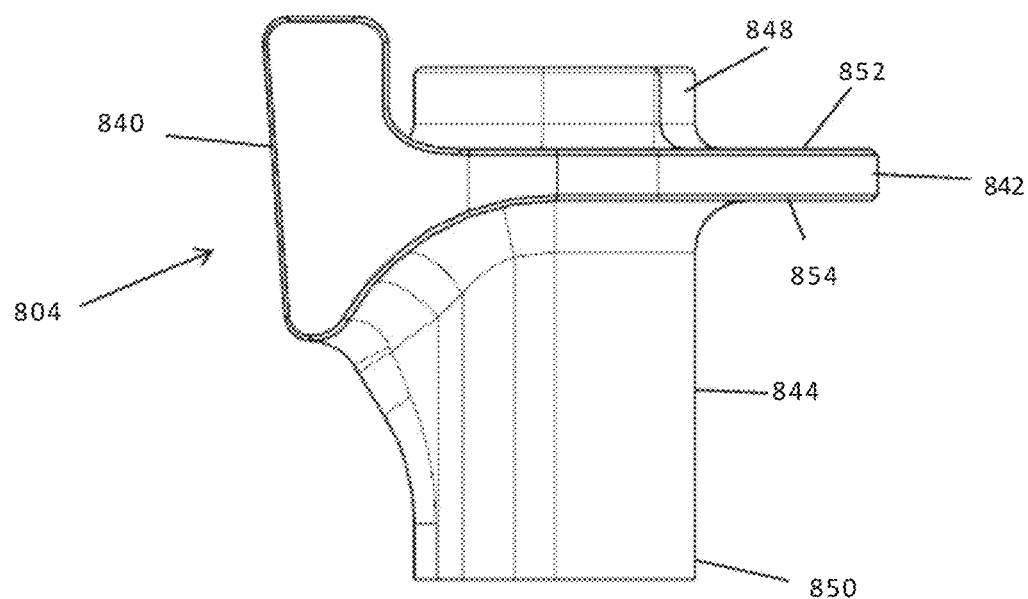
FIG. 12A is a side view representatively illustrating a lower member of the mounting bracket in accordance with exemplary embodiments of the present technology.
Figure 12B:
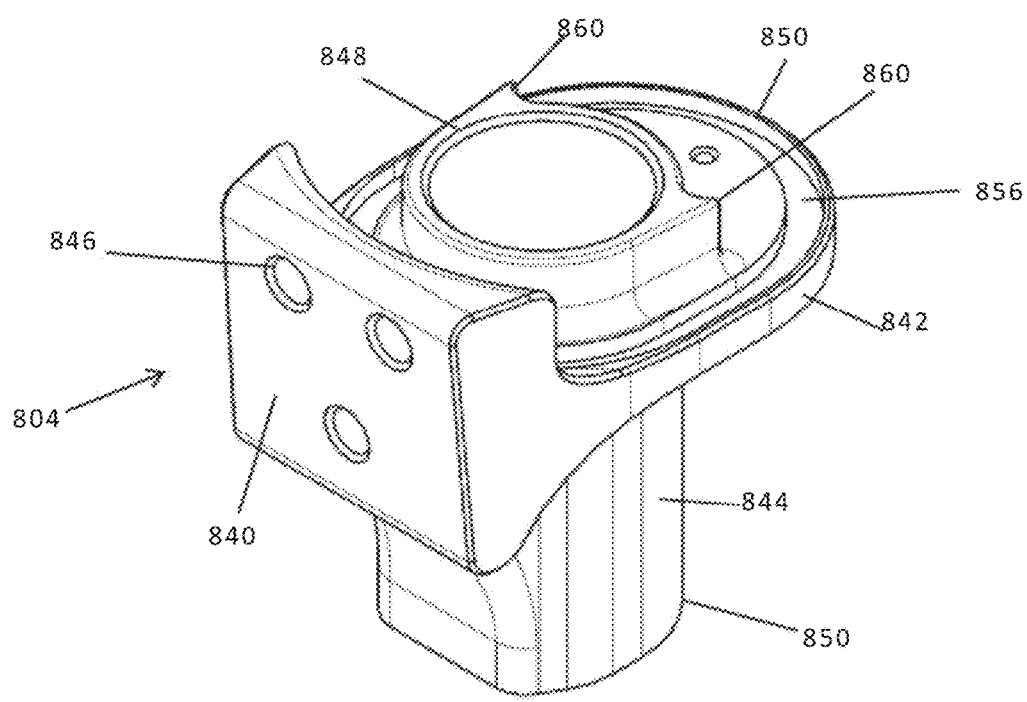
FIG. 12B is a perspective view representatively illustrating the lower member of the mounting bracket in accordance with exemplary embodiments of the present technology.
Figure 13:
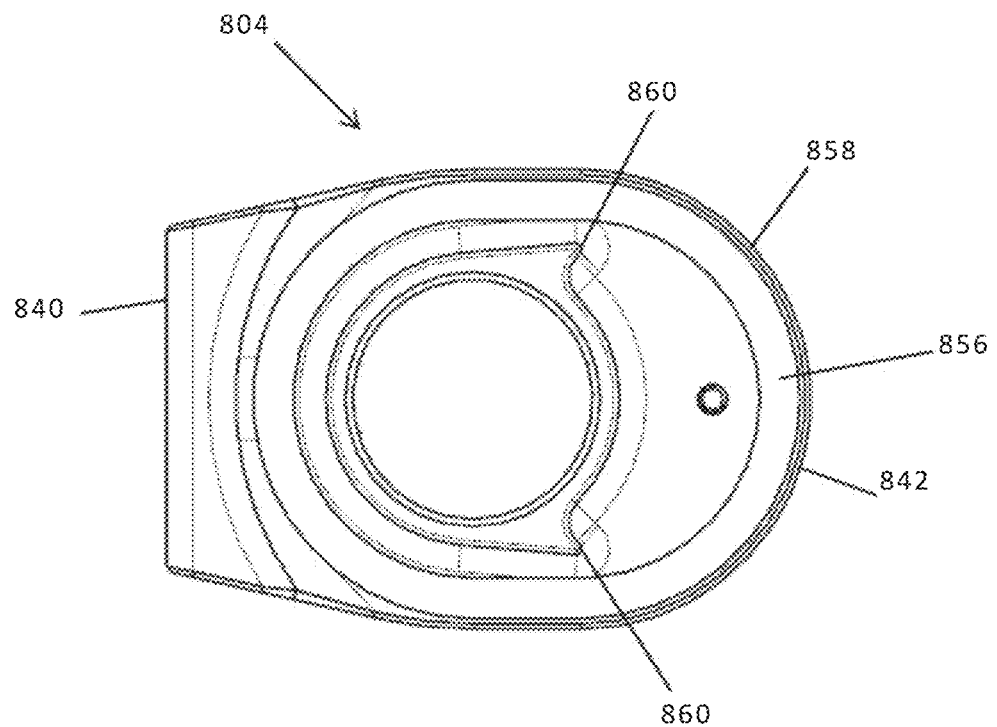
FIG. 13 is a top view representatively illustrating the lower member of the mounting bracket in accordance with exemplary embodiments of the present technology.

Referring now to FIGS. 12-13, in various embodiments, the lower member 804 may comprise a mounting portion 840, a lower flange 842, and a mating portion 844. The mounting portion 840 may be located at a rear edge of the lower flange 842. The mounting portion 840 may comprise at least one threaded aperture 846 used to couple the mounting bracket 800 to the prosthetic foot 100. (See FIGS. 8 and 9) In one embodiment, the mounting portion 840 comprises 3 threaded apertures 846 which receive bolts 864 to couple the mounting bracket 800 to the prosthetic foot 100.

In various embodiments, as shown in FIG. 9, an upper end 862 of the prosthetic foot 100 may be connected to the mounting portion 840 of the lower member 804 via mechanical connection whereby fasteners 864 are received within apertures (not shown) residing in the upper end 862 of the prosthetic foot 100 and the mounting portion 840 of lower member 804. While a bolted connection is shown any mechanical connection may be contemplated, such as screws, rivets, and the like. The bolted connection materials may comprise Titanium or any other suitable material. Other types of material may comprise mild steel, alloy steel, high strength stainless steel such as 13-8, and alloy aluminum such as the 2000 and 7000 series.

Figure 14A:
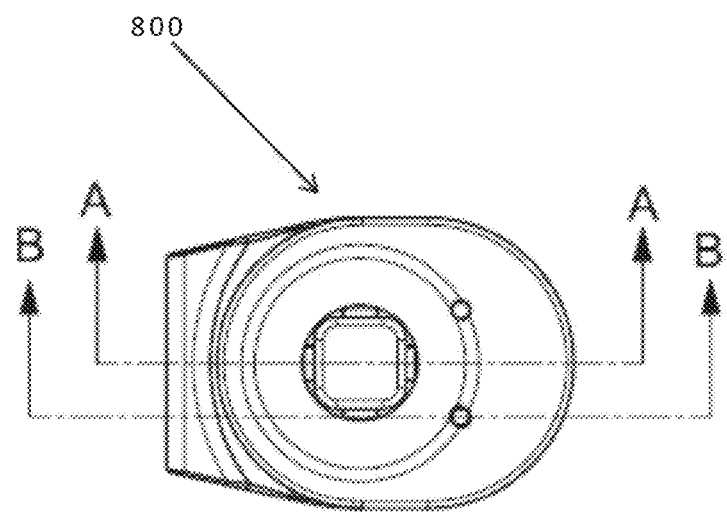
FIG. 14A is a top view representatively illustrating the mounting bracket in accordance with exemplary embodiments of the present technology.
Figure 14B:
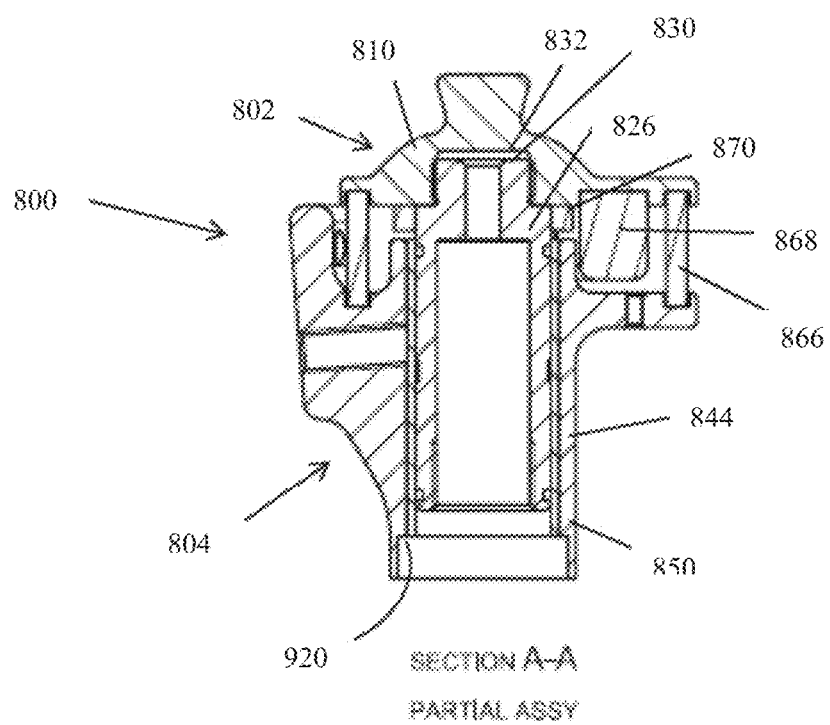
FIG. 14B is a partial, side, cross-section view taken along the line A-A in FIG. 14A representatively illustrating the mounting bracket in accordance with exemplary embodiments of the present technology.
Figure 15:
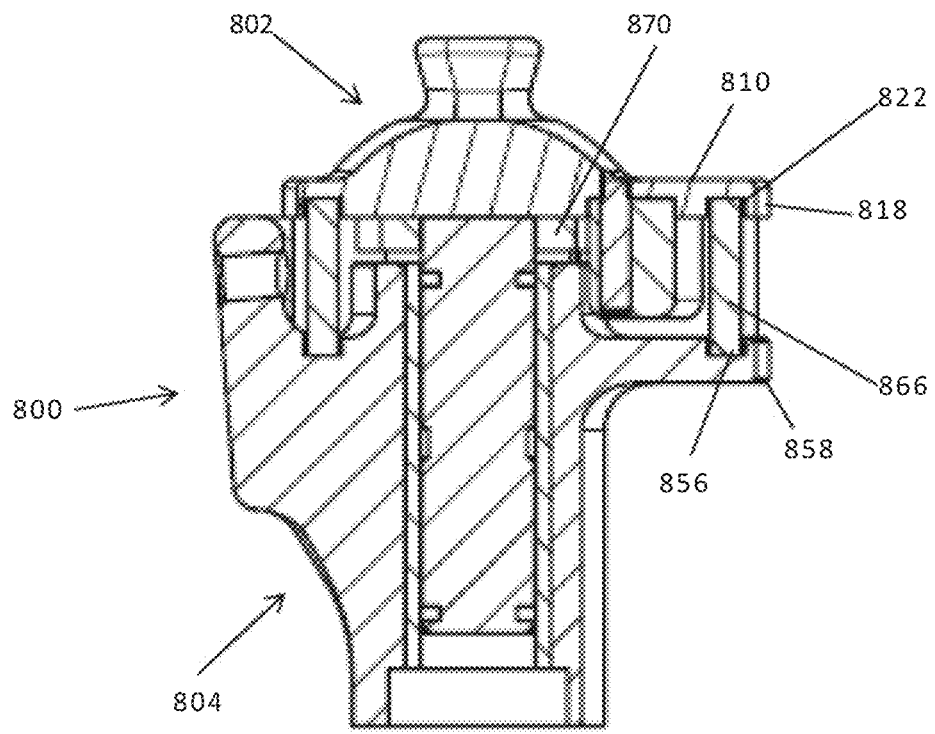
FIG. 15 is a partial, side, cross-section view taken along the line B-B in FIG. 14A representatively illustrating the mounting bracket in accordance with exemplary embodiments of the present technology.
Figure 16:
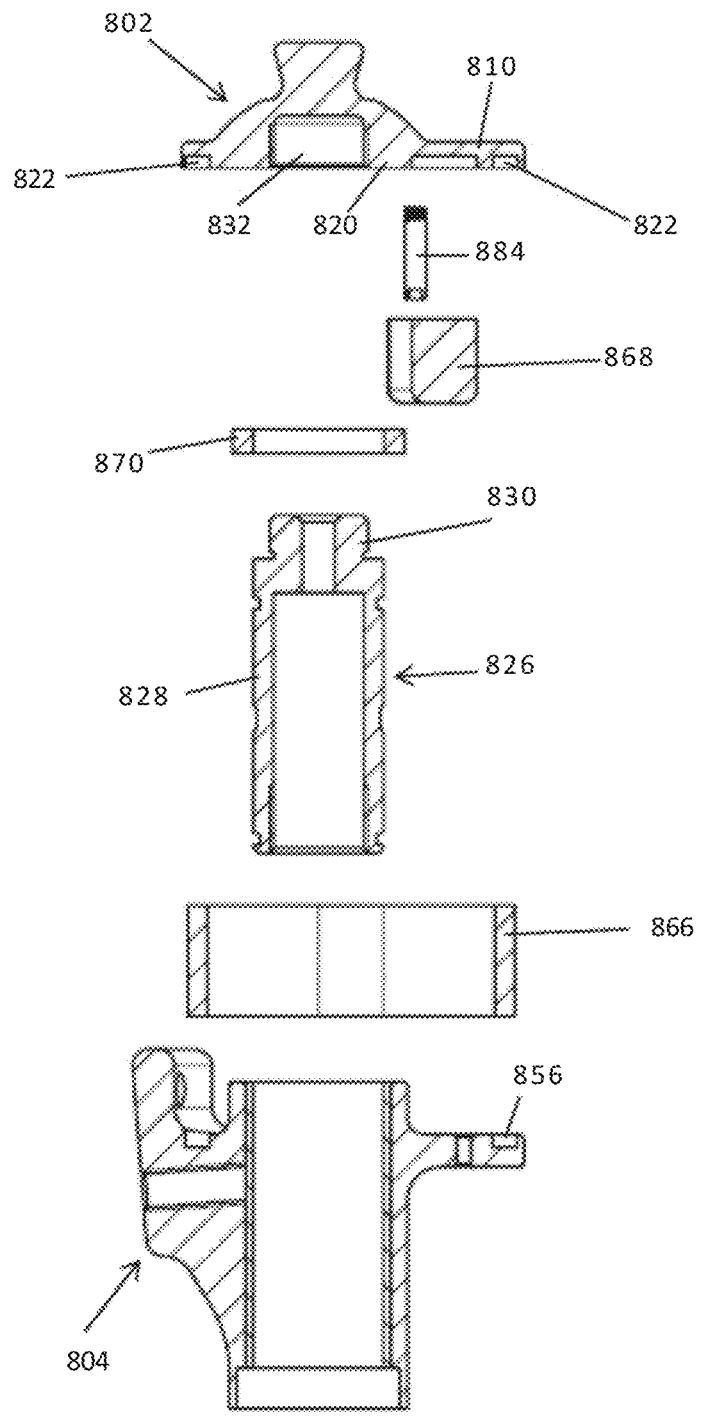
FIG. 16 is a partial, exploded, side, cross-section view taken along the line A-A in FIG. 14A representatively illustrating the mounting bracket in accordance with exemplary embodiments of the present technology.

The mating portion 844 of the lower member 804 may comprise an upper collar 848 and a lower collar 850. The upper collar 848 depends upwardly from an upper surface 852 of the lower flange 842 while the lower collar 850 depends downwardly from a lower surface 854 of the lower flange 842. As shown in FIGS. 12A-B and 14B, the upper and lower collars 848, 850 of the mating portion 844 combine to receive the cylindrical collar 828 of the mating post 826 of the upper member 802 when the upper and lower members 802, 804 are connected. As shown in FIGS. 12A, 12B, 13 and 15, the upper surface 852 of the lower flange 842 may comprise a recessed channel 856 and a lip 858 surrounding a portion of the perimeter.

In various embodiments, the lower member 804 may comprise a pair of stops 860. The stops 860 serve to limit rotation of the upper member 802 with respect to the lower member 804 during use as will be discussed in detail below.

In another embodiment, shown in FIG. 33, a lower member 934 is provided without any stops. In this embodiment, the bumper 868 may function as a compression bumper and not a torsion bumper. The remainder of the lower member 934 is similar to lower member 804.

Referring now to FIGS. 9, 10, 16 and 19 in various embodiments, the compression torsion joint 806 may comprise an elastomeric ring 866. In various embodiments, the compression torsion joint 806 may comprise a bumper 868. In various embodiments, the compression torsion joint 806 may comprise a compression collar 870. In one embodiment, the compression torsion joint 806 may comprise a combination of the elastomeric ring 866, the bumper 868, and the compression collar 870.

Figure 19:
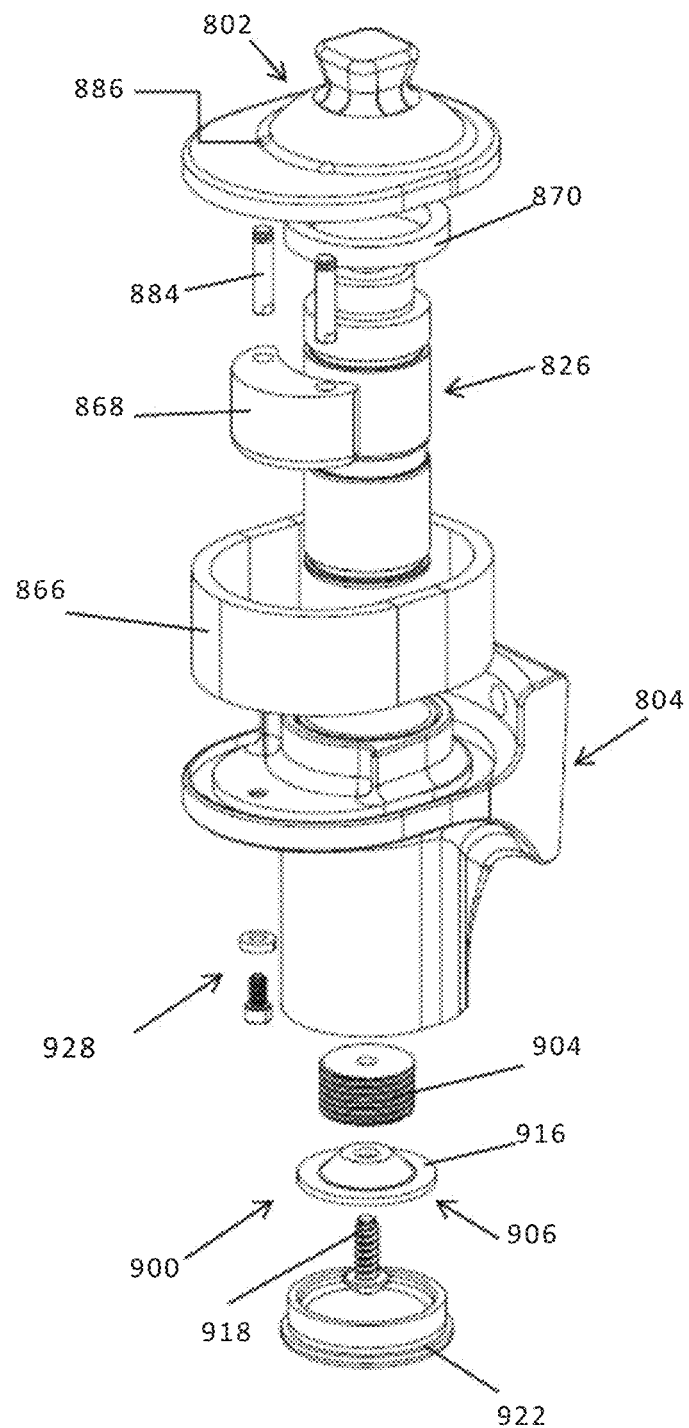
FIG. 19 is an exploded, perspective view representatively illustrating the mounting bracket of FIG. 10 in accordance with exemplary embodiments of the present technology.
Figure 22A:
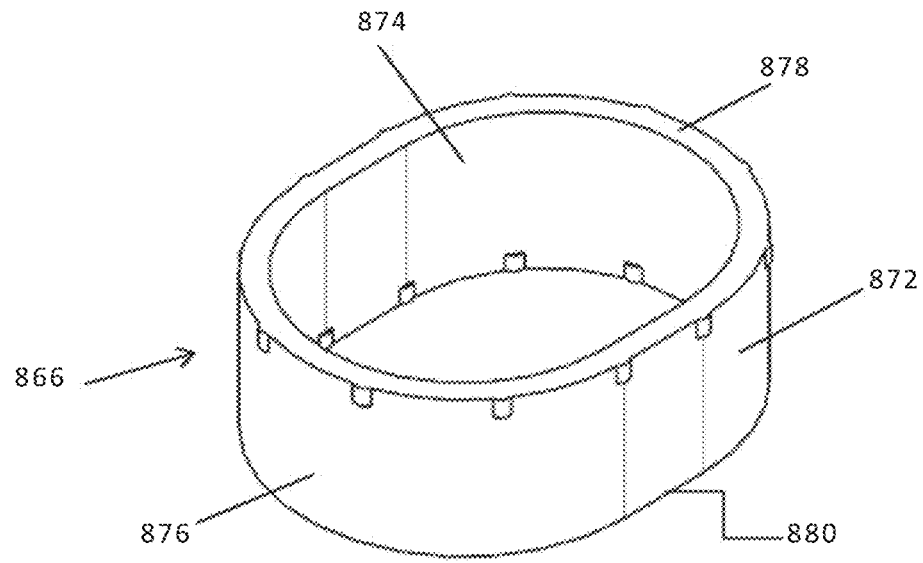
FIG. 22A is a perspective view representatively illustrating an elastomeric ring of the mounting bracket in accordance with exemplary embodiments of the present technology.
Figure 22B:
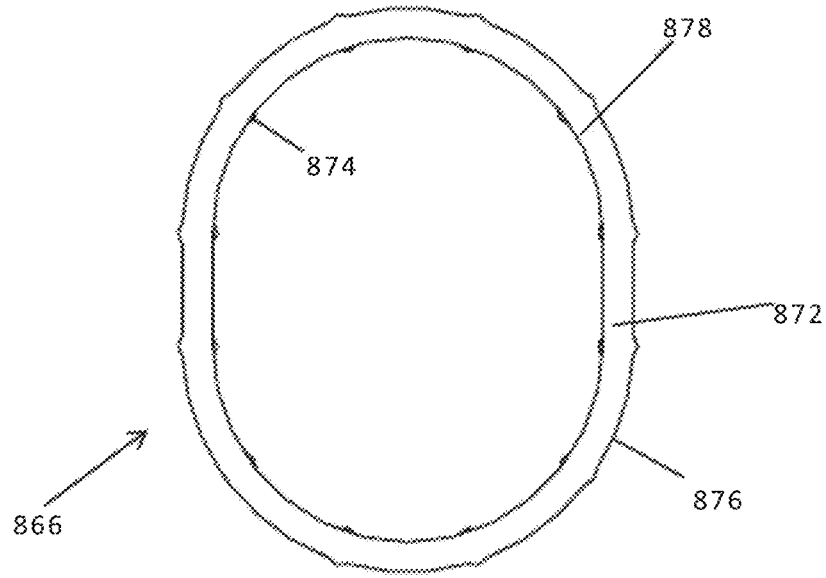
FIG. 22B is a top view representatively illustrating the elastomeric ring of the mounting bracket in accordance with exemplary embodiments of the present technology.

Referring to FIGS. 19, 22A and 22B, the elastomeric ring 866 may comprise a wall 872 with inner 874, outer 876, upper 878, and lower 880 surfaces. In one embodiment, shown in FIGS. 22A and 22B, the inner surface 874 of the wall 872 comprises a substantially smooth surface. In one embodiment, the inner surface 874 may comprise a ridged surface, a surface with raised portions, and or a wall with varying thickness. In one embodiment, the inner and outer surfaces 874, 876 may be curved from the upper 878 to lower surface 880, and/or convex with respect to the center of the elastomeric ring 866. In one embodiment, the outer surface 876 may be curved, and/or convex with respect to the center of the elastomeric ring 866. Referring now to FIGS. 11C, 13, 15, and 22A the upper surface 878 of the elastomeric ring 866 may be received in the channel 822 in the upper flange 810 in the upper member 802. The outer surface 876 generally abuts the lip 818 of the upper flange 810 of the upper member 802. The lower surface 880 of the elastomeric ring 866 may be received in the channel 856 in the lower flange 842 in the lower member 804. The outer surface 876 generally abuts the lip 858 of the lower flange 842 of the lower member 804.

Figure 28A:
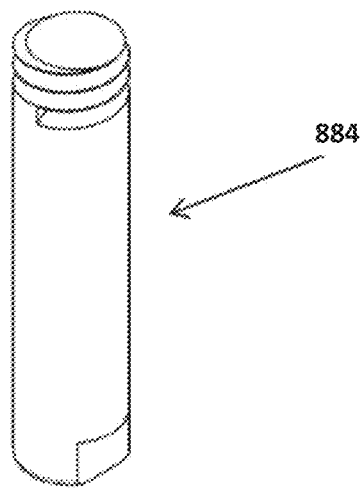
FIG. 28A is a perspective view representatively illustrating a pin of the mounting bracket in accordance with exemplary embodiments of the present technology.
Figure 28B:
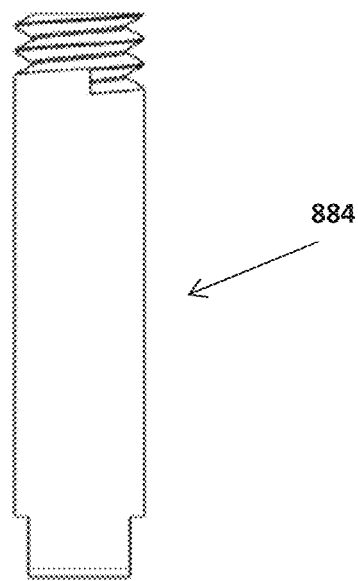
FIG. 28B is a side view representatively illustrating the pin of the mounting bracket in accordance with exemplary embodiments of the present technology.

In one embodiment, shown in FIGS. 17, 19, and 23A-C, the compression torsion joint 806 may comprise a bumper 868. In one embodiment, the bumper 868 may comprise a compression/torsion bumper. In another embodiment, the bumper 868 may comprise a compression bumper. The bumper 868 may be crescent shaped and received within the crescent-shaped recess 824 of the upper flange 810 of the lower member 804 (See FIG. 11C). An upper surface 881 of the bumper 868 may be received in and bonded within the crescent-shaped recess 824 in the manner described below with respect to the elastomeric ring 866. In use, a lower surface 882 of the bumper 868 will contact the upper surface 852 of the lower flange 842 thereby only allowing a limited amount of vertical movement of the upper member 802 with respect to the lower member 804 (See FIGS. 12A-B). The bumper 868 limits the vertical movement while the elastomeric ring 866 provides vertical shock absorption during the gate cycle and while standing. In one embodiment, the 868 may comprise a pair of holes 883 that receive pins 884 (See FIGS. 28A-B). The pins 884 may comprise at least partially threaded shafts that are received in a pair of threaded holes 886 within the upper member 802. In one embodiment, the stops 860 in conjunction with the bumper 868 and the pins 884 serve to limit the torsional rotation of the upper member 802 with respect to the lower member 804 during use. When used in combination with the stops 860, the bumper 868 is a compression/torsion bumper. In the embodiment discussed above, where the stops are absent from the lower member, the bumper 868 may function as a compression bumper and not a torsion bumper.

Figure 17:
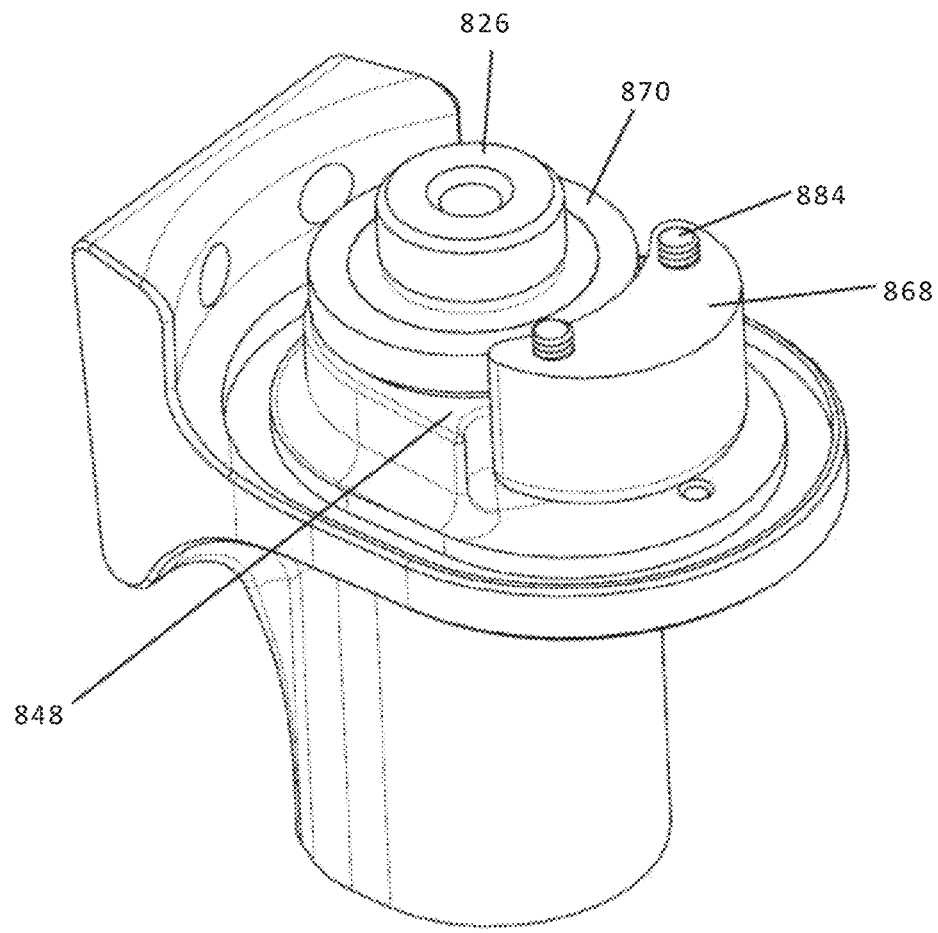
FIG. 17 is a perspective view representatively illustrating the lower member of the mounting bracket with a compression collar and a compression/torsion bumper in accordance with exemplary embodiments of the present technology.
Figure 18:
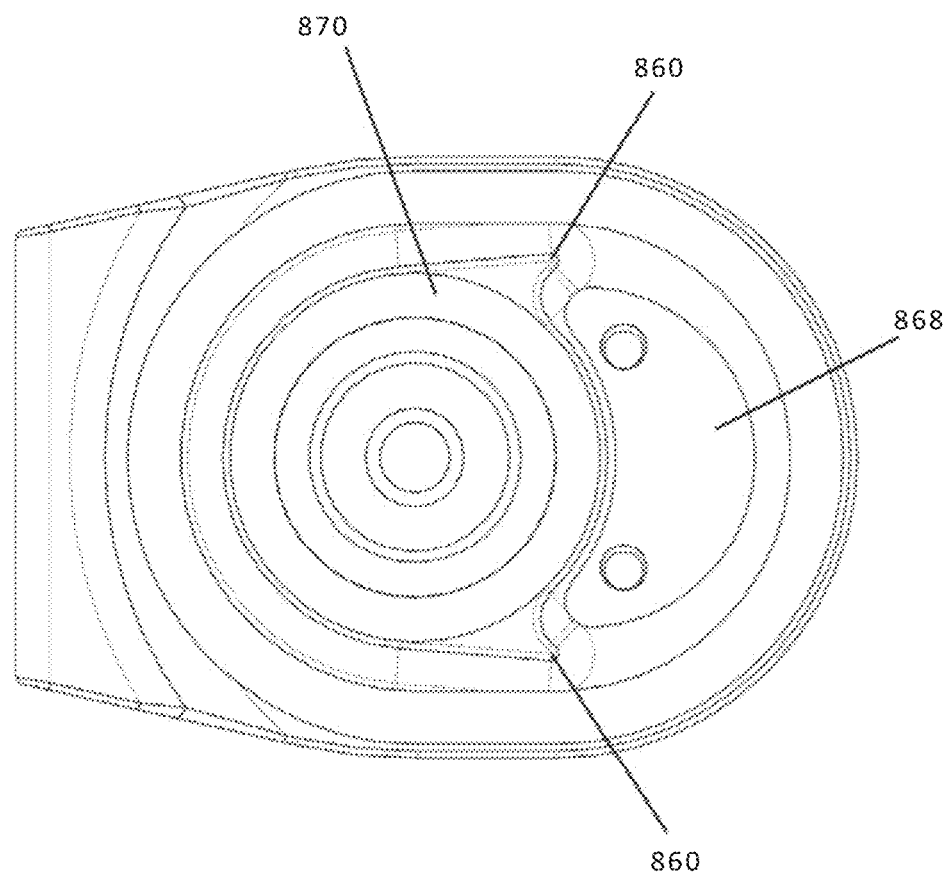
FIG. 18 is a top view representatively illustrating lower member of the mounting bracket with a compression collar and a compression/torsion bumper in accordance with exemplary embodiments of the present technology.
Figure 24A:
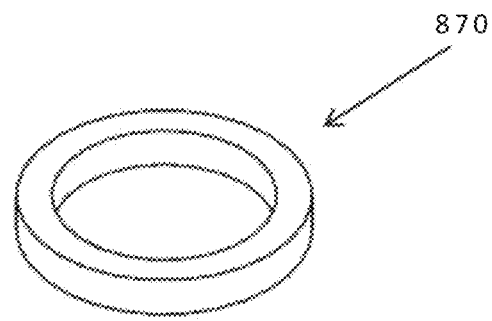
FIG. 24A is a perspective view representatively illustrating a compression collar of the mounting bracket in accordance with exemplary embodiments of the present technology.
Figure 24B:
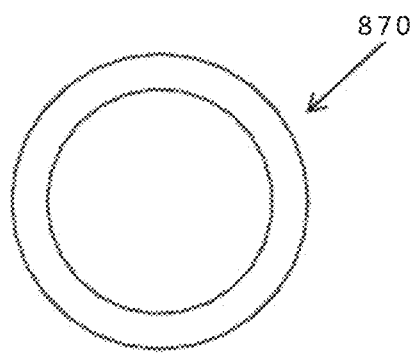
FIG. 24B is a top view representatively illustrating the compression collar of the mounting bracket in accordance with exemplary embodiments of the present technology.
Figure 25:
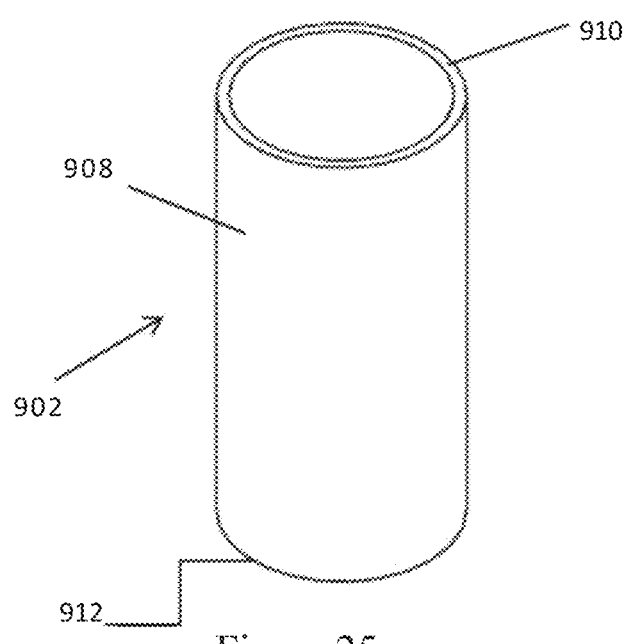
FIG. 25 is a perspective view a sleeve of the mounting bracket in accordance with exemplary embodiments of the present technology
Figure 26A:
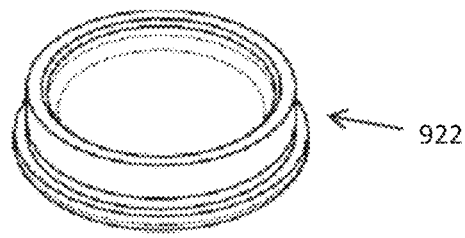
FIG. 26A is a perspective view representatively illustrating a cap of the mounting bracket in accordance with exemplary embodiments of the present technology.
Figure 26B:
FIG. 26B is a side view representatively illustrating the cap of the mounting bracket in accordance with exemplary embodiments of the present technology.
Figure 26C:
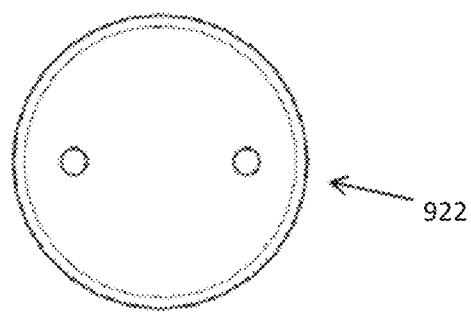
FIG. 26C is a bottom view representatively illustrating the cap of the mounting bracket in accordance with exemplary embodiments of the present technology.
Figure 27A:
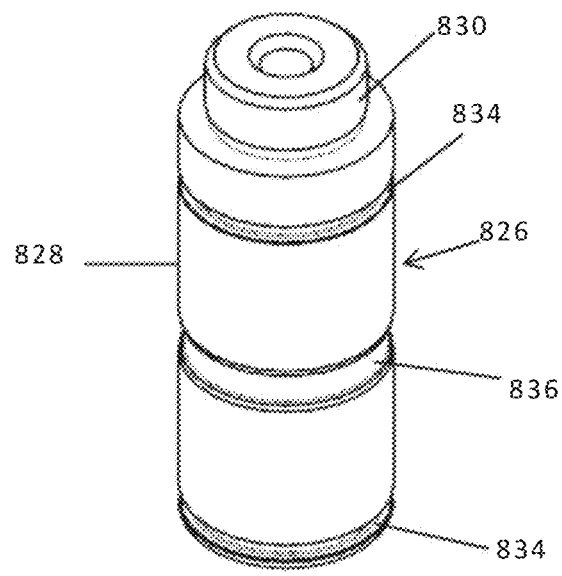
FIG. 27A is a perspective view representatively illustrating a mating post of the mounting bracket in accordance with exemplary embodiments of the present technology.
Figure 27B:
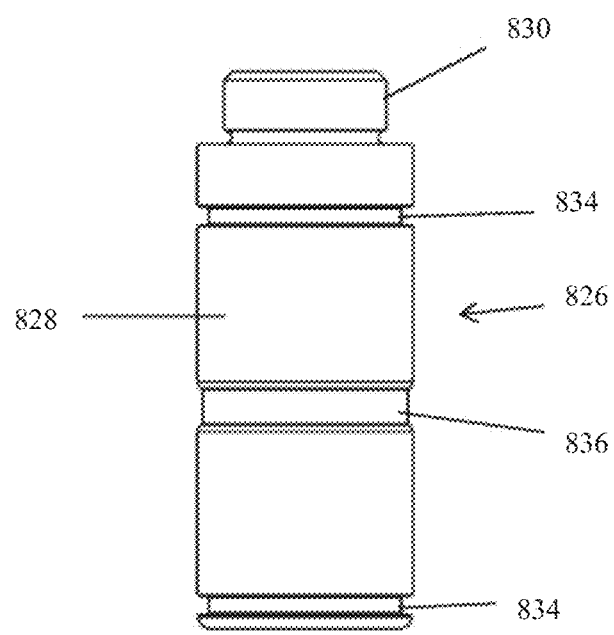
FIG. 27B is a side view representatively illustrating the mating post of the mounting bracket in accordance with exemplary embodiments of the present technology.

In various embodiments, as shown in FIGS. 17, 19, and 24 and a compression collar 870 may be received on the cylindrical collar 826 and abut the lower surface 820 of the upper flange 810. In one embodiment, when assembled, a gap may exist between the lower surface of the compression collar 870 and an upper surface of the upper collar 848. A gap may also exist between a lower surface of bumper 868 and the upper surface of the lower flange 842. In another embodiment, when assembled, the lower surface of the compression collar 870 may abut an upper surface of the upper collar 848.

Figure 29:
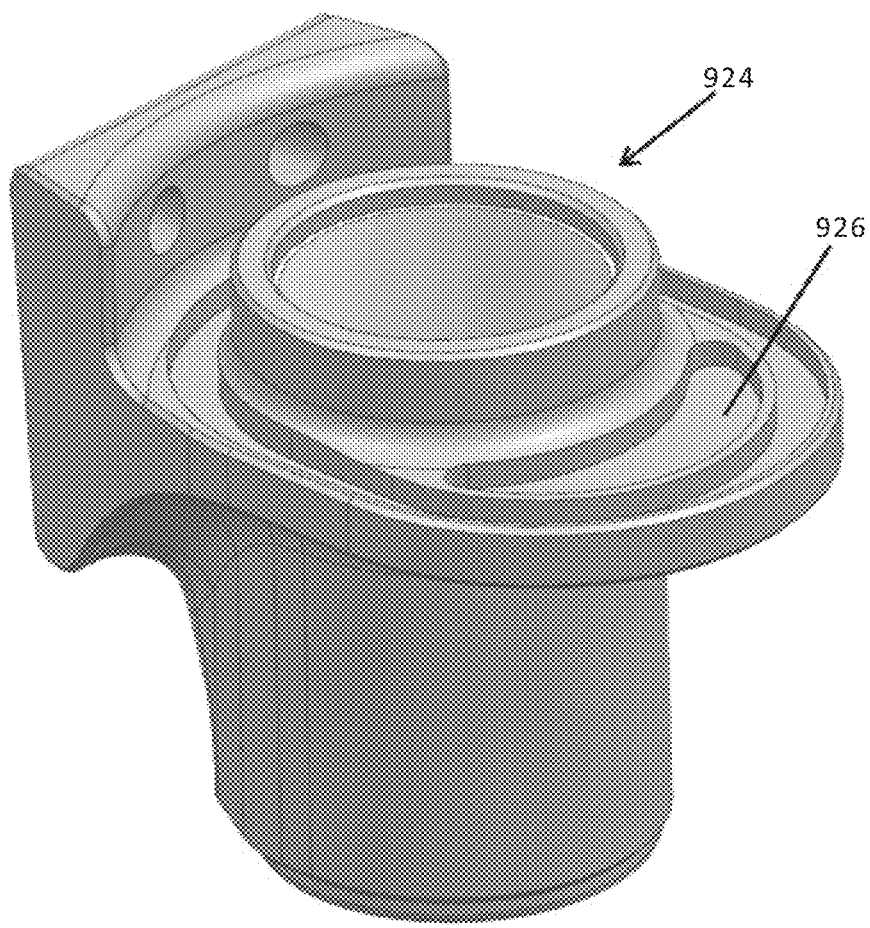
FIG. 29 is a perspective view representatively illustrating an additional embodiment of a lower member of the mounting bracket in accordance with exemplary embodiments of the present technology.
Figure 30:
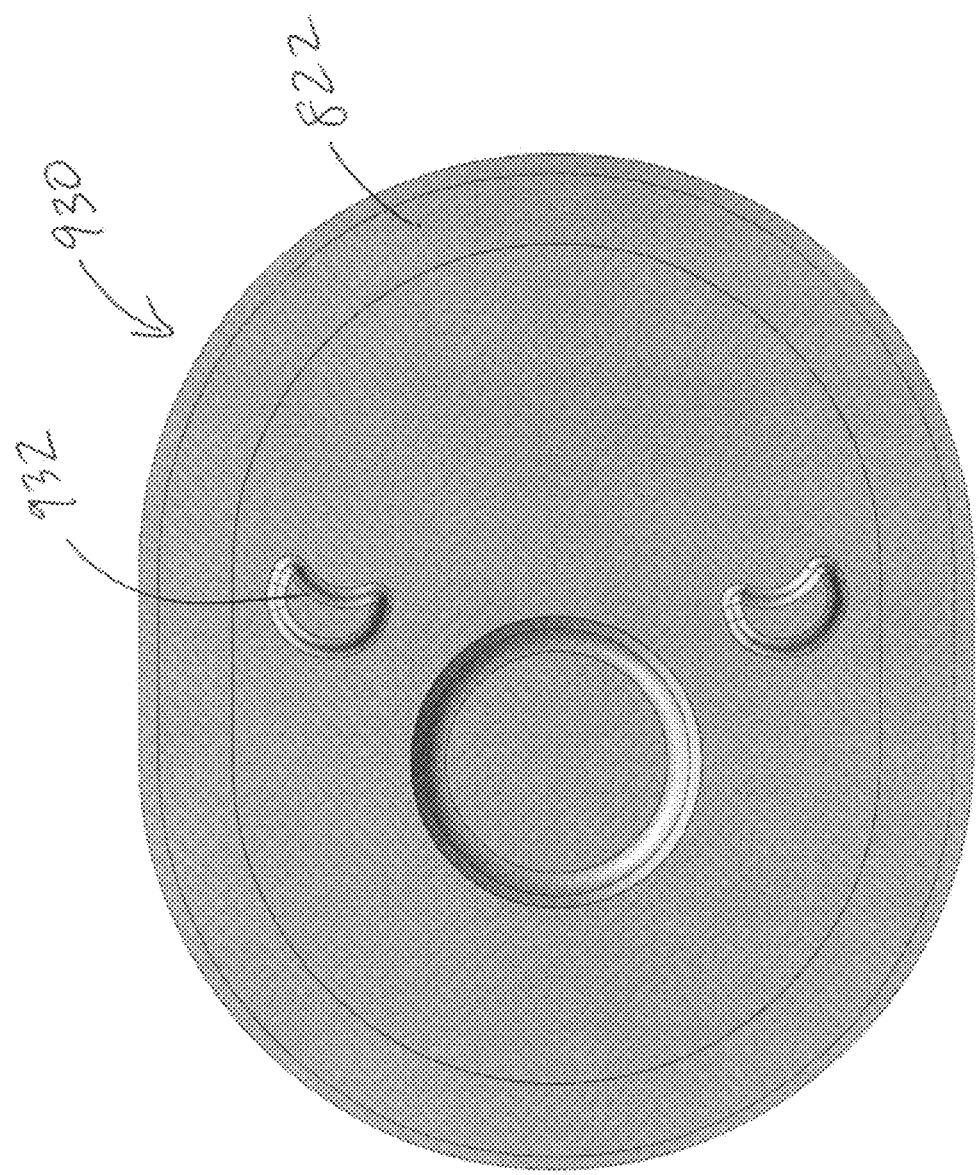
FIG. 30 is a bottom view representatively illustrating an additional embodiment of an upper member of the mounting bracket in accordance with exemplary embodiments of the present technology.

In another embodiment, referring to FIG. 29, a lower member 924 is shown having a crescent-shaped recess 926. The lower surface 882 of the bumper 868 may be received in and bonded within the crescent-shaped recess 926 in the manner described below with respect to the bonding of the elastomeric ring 866. Referring to FIGS. 30 and 31, in one embodiment, an upper member 930 is shown comprising a pair of stops 932 and channel 822. In this embodiment, the bumper 868 is a compression/torsion bumper. The remainder of upper member 930 is similar to the upper member 802 but without a crescent-shaped recess. This embodiment, shown in FIGS. 29-31, operates similarly to the embodiment discussed above of the lower member 804 having the stops 860 and the upper member 802 having the crescent-shaped recess 824.

Referring now to FIGS. 9 and 12A-B, in various embodiments, the mounting bracket 800 may comprise a washer plate 888. The washer plate 888 may be used when coupling the mounting bracket 800 to the upper end 862 of the prosthetic foot 100. The washer plate 888 may comprise the same number of apertures as the upper end 862 of the prosthetic foot 102 and the mounting portion 840 of the lower member 804. The washer plate 888 is designed to spread the load and reduce the stress concentration across the surface of the upper end 862 of the prosthetic foot 100. In another embodiment, the prosthetic foot 100 may also utilize standard washer configurations.

Referring now to FIGS. 19-21 and 25, in various embodiments, the mounting bracket 800 may comprise a retention system 900. The retention system 900 is utilized as a failsafe to ensure that the upper member 802 does not disconnect from the lower member 804 in the situation where the bond on the elastomeric ring 866 that connects the upper and lower members 802, 804 fails. In various embodiments, the retention system 900 may comprise a sleeve 902, a plug 904, and a connector 906.

In various embodiments, the sleeve 902 may comprise a cylindrical wall 908 and first and second ends 910, 912. The sleeve 902 fits within the mating portion 844 of the lower member 804. The sleeve 902 may be inserted at a lower end of the lower member 804 and may extend along the length of the mating portion 844. The first end 910 of the sleeve 902 may abut a lip formed in the interior of the upper collar 848 of the lower member 804. The lip is configured to retain the first end 910 within the mating portion 884.

In various embodiments, the plug 904 contains threads which are received within internal threads located in the internal wall 914 in the cylindrical collar 828 of the mating post 826. The connector 906 may be used in conjunction with the mating post 826, which is received within the sleeve 902, to couple the upper member 802 to the lower member 804. The sleeve 902 may comprise a low-friction material that facilitates smooth movement between the upper and lower members 802, 804. The connector 906 may comprise a retention washer 916 and a retention connector 918. The retention connector 918 is used in conjunction with the retention washer 916 and is received within a threaded aperture in the plug 904. When tightened, the retention connector 918 seats the retention washer 916 against an internal shelf 920 in the lower member 804 (See FIGS. 14B, 20B, and 21). In one embodiment, the retention connector 918 is a screw.

Figure 20A:
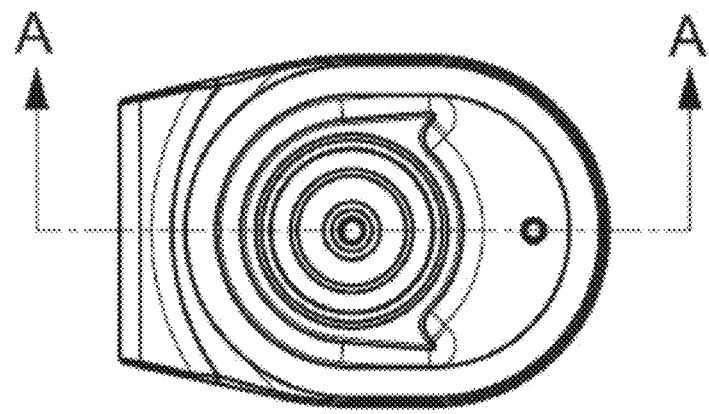
FIG. 20A is a top, partially assembled, lower member view representatively illustrating portions of the mounting bracket in accordance with exemplary embodiments of the present technology.
Figure 20B:
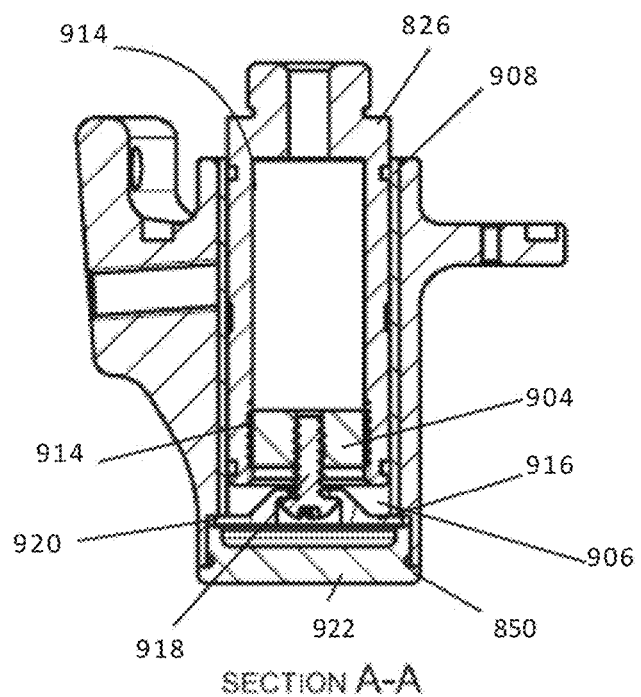
FIG. 20B is a partial, side, cross-section view taken along the line A-A in FIG. 20A representatively illustrating portions of the mounting bracket in accordance with exemplary embodiments of the present technology.
Figure 21:
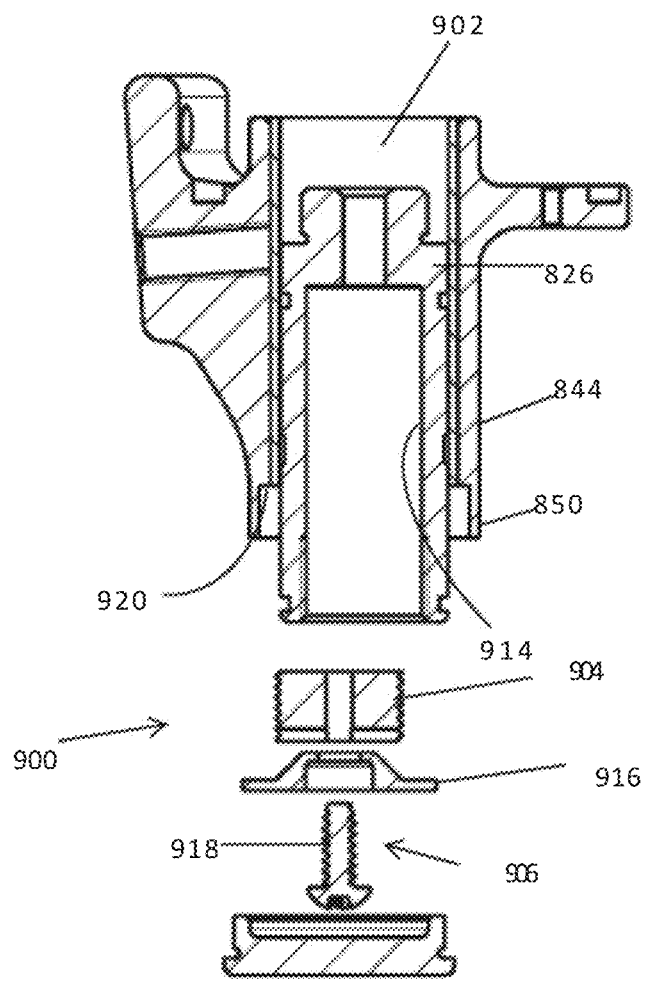
FIG. 21 is a partial, exploded side, cross-section view taken along the line A-A in FIG. 20A representatively illustrating portions of the mounting bracket in accordance with exemplary embodiments of the present technology

In various embodiments, referring now to FIGS. 19, 20B, and 21 the retention system 900 may comprise a cap 922. The cap 922 retains the second end 912 of the sleeve 902 within the lower collar 850 of the mating portion 844. The cap 922 may be press fit or may contain threads that mate with internal threads (not shown) in the lower collar 850 of the mating portion 844. In use, the cylindrical collar 828 of the mating post 826 is received within the sleeve 902, which is received in the upper and lower collars 848, 850 of the mating portion 844 when the upper and lower members 802, 804 are connected.

The cap 922 may butt up against the retention washer 916 pressing it against the second end 912 of the sleeve 902. The cap 922 also seats the spacer within the mating portion 844 and keeps dirt, sand, or small objects from entering the mating portion 844 of the lower member 804. Objects such as small rocks or sand could wear away the moving internal members eventually causing damage or failure.

The sleeve 902 may be made from any suitable low-friction material. In one embodiment the low friction sleeve is made from plastic to allow for smooth movement between the components of the prosthetic foot. In one embodiment a low coefficient plastic bushing material may be used.

In various embodiments, the mounting bracket 800 may comprise a vent assembly 928. In one embodiment the vent assembly 928 may comprise a screw, a washer and an aperture in the lower member 804. The screw is received within the aperture in the lower member 804. Removal of the screw from the aperture in the vent assembly 928 may be used to equalize pressure (during adhesive bond cure) inside the mounting bracket 800 with the ambient surrounding pressure. Without this vent assembly 928, pressure builds up inside the cavity in mounting bracket 800 and forces the metal components to partially separate from the elastomeric ring 866.

In use under load, a lower surface of the bumper 868 will contact the upper surface of the lower flange 842 in conjunction with compression collar 870 thereby only allowing a limited amount of vertical movement of the upper member 802 with respect to the lower member 804. The compression collar 870 limits vertical movement. The bumper 868 limits the vertical and torsional movement when used with an upper or lower member having stops. The bumper 868 limits the vertical movement when used with an upper or lower member without stops. The elastomeric ring 866 provides vertical shock absorption and torsional stability during the gate cycle and while standing.

The mounting bracket 800 provides a multi-phase system. When the initial load is applied to the prosthetic foot 100, the elastomeric ring 866 provides both a soft resistance for vertical compression and torsional rotation. Once a larger load is applied, the lower surface 882 of the bumper 868 will contact an upper surface 852 of the lower flange 842 and the lower surface of the compression collar 870 will contact an upper surface of the upper collar 848, thereby only allowing a limited amount of vertical movement of the upper member 802 with respect to the lower member 804. The bumper 868 and compression collar 870 limit the vertical movement while the elastomeric ring 866 provides vertical shock absorption during the gate cycle and while standing.

When a greater torsional load is applied, the elastomeric ring 866 gives increasingly stiff torsional stability until the bumper 868 contacts the stops 860 to limit the amount of torsional rotation. In one embodiment, the bumper 868 and the stops 860 serve to restrict the torsional rotation approximately 5-10 degrees. In one embodiment, the bumper 868 and the stops 860 serve to restrict the torsional rotation approximately plus or minus 8 degrees.

In various embodiments, the elastomeric ring 866 may comprise a lower durometer than the bumper 868 and compression collar 870 thereby providing an initial soft resistance to vertical load and torsional rotation. The higher durometer compression collar 870 provides a greater resistance during high vertical loads. The compression collar 870 can comprise different heights that affect the sensation of the mounting bracket 800 during vertical compression. If the compression collar 870 is taller, it can make contact before the bumper 868. The higher durometer bumper 868 provides a greater resistance during high loads both vertically and torsionally. Thus, the system described above may provide multi-phase resistance to vertical loading and torsional rotation based on the user's needs.

According to various embodiments the upper and lower members 802, 804 may be made from Titanium (any type) or any other suitable material. In one embodiment the upper member 802 may comprise titanium. In one embodiment the lower member 804 may comprise alloy aluminum. Some other types of material that may be used for the upper and lower members 802, 804 comprise mild steel, alloy steel, steel, high strength stainless steel such as 13-8, alloy aluminum such as the 2000 and 7000 series, and any suitable composite material.

In various embodiments, the upper and lower members 802, 804 described above can be an integral piece or multiple pieces joined together by any suitable method. In some embodiments, depending on the type of material, the upper and lower members 802, 804 may be fabricated by milling, casting, forging, powdered metal, and the like. In one embodiment, the upper and lower members 802, 804 may be fabricated on a titanium CNC milling machine. More specifically, in one embodiment the upper and lower members 802, 804 may be unitary made from alloy aluminum fabricated using a CNC milling machine. In other embodiments, the aluminum, titanium, magnesium or other suitable material for the upper and lower members 802, 804 may be fabricated using a CNC milling machine. In other embodiments, the aluminum, titanium, magnesium or other suitable for the upper and lower members 802, 804 may be fabricated by casting, forging, powdered metal, and the like. In other embodiments, a chrome moly, steel, or other suitable material for the upper and lower members 802, 804 can be made from multiple pieces and coupled together by welding or any other suitable method According to various embodiments and referring to FIGS. 10-12, and 22 the upper and lower members 802, 804 may be coupled by the elastomeric ring 866. The elastomeric ring 866 may comprise any rubber, polyurethane, and/or elastomeric materials. The elastomeric ring 866 may be bonded to the upper and lower members 802, 804 using an adhesive. The upper surface 878 of the elastomeric ring 866 may be received in and bonded within the channel 822 in the upper flange 810 in the upper member 802. The lower surface 880 of the elastomeric ring 866 may be received in and bonded the channel 856 in the lower flange 842 in the lower member 804. The elastomeric ring 866 may act as a shock for absorbing force on the downward strike during the user's stride.

In various embodiments, the elastomeric ring 866 may comprise an adhesive bonding and thus coupling the lower member to the upper member. Further, the adhesive bonding of the elastomeric ring 866 may produce distributed stresses. Though other modulus values are contemplated, and various moduli may be used as well, a stiffer adhesive is preferred compared to a flexible adhesive. The elastomeric ring 866 creates a space between the upper flange 810 of the upper member 802 and the lower flange 842 of the lower member 106. The adhesive may be commingled with the elastomeric ring 866.

The prosthetic foot 100 can be adjusted to accommodate a user in part by adjusting characteristics of the elastomeric ring 866 between the upper member 802 and lower member 804. For example, in various embodiments, the durometer of the elastomeric ring 866 can be increased for users with more heel strike force, which may be caused by additional weight or dynamic activity.

In various embodiments and as shown the elastomeric ring 866 and 868 may comprise an elastomeric material. The elastomeric material may comprise a general elastomeric material, polyurethane, natural rubber, a synthetic rubber, or various combinations of natural and synthetic rubber. The durometer of the elastomeric material of both the elastomeric ring 866 and bumper 868 may be varied to provide additional adjustment of the prosthetic foot. The elastomeric material of the elastomeric ring 866 and bumper 868 supports load. Further, since the elastomeric ring 866 couples the upper and lower members 802, 804, the members are capable of torsional rotation during use of the prosthetic foot 100. The adjustable durometer of the elastomeric material allows the adjustment of the spring rate of the elastomeric ring based on user needs such as activity level, compliance level, weight changes, and the like. For example, in various embodiments, the durometer of the elastomeric material can be increased for users with more heel strike force, which may be caused by additional weight of the user or dynamic activity of the user. Increased heel strike force also provides greater compression of the heel member. As stated above the elastomeric ring 866 may comprise a lower durometer than the bumper 868 thereby providing an initial soft resistance to vertical load and torsional rotation. The higher durometer bumper 868 provides a greater resistance during high loads both vertically and torsionally.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

The invention claimed is:

1. A mounting bracket for a prosthetic foot configured to attach to a residual limb, comprising:
   an upper member comprising an upper flange, a mating post, and a mounting portion configured to attach to the residual limb;
   a lower member comprising a mating portion, a lower flange, and a mounting portion configured to attach to the prosthetic foot, wherein the lower flange of the lower member comprises a pair of stops; and
   a compression torsion joint coupling the upper member to the lower member and configured to limit vertical movement and torsional movement of the upper member with respect to the lower member, comprising:
      an elastomeric ring configured to limit the vertical movement and torsional movement of the upper member with respect to the lower member; and
      a compression torsion bumper configured to limit the vertical movement and torsional movement of the upper member with respect to the lower member, wherein the compression torsion bumper contacts the stops to resist torsional movement of the upper member with respect to the lower member.

2. The mounting bracket of claim 1, wherein the mating post of the upper member is received within the mating portion of the lower member.

3. The mounting bracket of claim 1, wherein the upper flange and lower flange each comprise a channel adjacent to a perimeter of the upper flange and lower flange.

4. The mounting bracket of claim 1, wherein an upper surface of the elastomeric ring is received within the channel in the upper flange and a lower surface of the elastomeric rings is received in the channel in the lower flange.

5. The mounting bracket of claim 4, wherein the upper surface of the elastomeric ring is coupled to the channel in the upper flange and the lower surface of the elastomeric ring is coupled in the channel in the lower flange.

6. The mounting bracket of claim 1, wherein the compression torsion bumper is coupled to a lower surface of the upper flange of the upper member.

7. The mounting bracket of claim 6, wherein the compression torsion bumper is coupled to and received within a recess in the lower surface of the upper flange of the upper member.

8. The mounting bracket of claim 7, wherein the compression torsion bumper and the recess are crescent shaped.

9. The mounting bracket of claim 1, wherein the compression torsion bumper is an elastomer.

10. The mounting bracket of claim 1, wherein a space exists between a lower surface of the compression torsion bumper and an upper surface of the lower flange of the lower member.

11. The mounting bracket of claim 1, wherein the compression torsion bumper and the stops serve to restrict the torsional rotation to approximately 8 degrees.

12. The mounting bracket of claim 1, wherein the compression torsion bumper is coupled to an upper surface of the lower flange of the lower member.

13. The mounting bracket of claim 12, wherein the compression torsion bumper is coupled to and received within a recess in the upper surface of the lower flange of the lower member.

14. The mounting bracket of claim 13, wherein the upper flange of the upper member comprises a pair of stops, wherein the compression torsion bumper contacts the stops to resist torsional movement of the upper member with respect to the lower member.

15. The mounting bracket of claim 1, wherein the compression torsion joint comprises a compression collar received on the mating post of the upper member and abuts a lower surface of the upper flange of the upper member.

16. The mounting bracket of claim 1, wherein the compression torsion joint comprises a compression bumper configured to limit the vertical movement of the upper member with respect to the lower member.

17. The mounting bracket of claim 1, further comprising a retention system comprising:
   a cylindrical sleeve inserted within the mating portion of the lower member and configured to receive the mating post of the upper member to provide smooth vertical and torsional movement between the mating post of the upper member and the mating portion of the lower member;

a plug coupled within a lower end of the mating post of the upper member; and a connector coupled to the plug and configured to contact a lower end of the lower member to attach the upper member to the lower member.

18. A mounting bracket for a prosthetic foot configured to attach to a residual limb, comprising:
an upper member comprising:
an upper flange with a channel;
a mating post; and
a mounting portion configured to attach to the residual limb;
a lower member comprising:
a lower flange with a channel, wherein the lower flange of the lower member comprises a pair of stops;
a mating portion configured to receive the mating post; and
a mounting portion configured to attach to the prosthetic foot;
a compression torsion joint coupling the upper member to the lower member and configured to limit vertical movement and torsional movement of the upper member with respect to the lower member, comprising:
an elastomeric ring having an upper surface coupled to the channel of the upper flange and a lower surface coupled to the channel of the lower flange; and
a compression torsion bumper coupled to the upper flange of the upper member, wherein the compression torsion bumper contacts the stops to resist torsional movement of the upper member with respect to the lower member; and
a retention system comprising:
a cylindrical sleeve inserted within the mating portion of the lower member and configured to receive the mating post of the upper member to provide smooth vertical and torsional movement between the mating post of the upper member and the mating portion of the lower member;
a plug coupled within a lower end of the mating post of the upper member; and
a connector coupled to the plug and configured to contact a lower end of the lower member to attach the upper member to the lower member.

19. The mounting bracket of claim 18, further comprising a pair of pins coupled to the upper member, extending within the compression torsion bumper, and configured to resist torsional movement of the upper member with respect to the lower member.

20. A prosthetic foot for use within a foot shell and configured to attach to a residual limb, comprising:
a resilient bottom member comprising a front end, a rear end, and having no inflection point, wherein a center point of a radius of curvature of the front end of the resilient bottom member is above the resilient bottom member, and the rear end of the resilient bottom member is straight;
a resilient top member comprising a front end and a rear end, wherein the front end of the resilient top member is connected to the front end of the resilient bottom member at a connection point, wherein the connection point is connected to an upper side of the rear end of the resilient top member, and wherein the resilient top member is positioned over the resilient bottom member;
a bumper member directly attached to an underside of the rear end of the resilient top member, wherein the bumper member is detached from the upper side of the rear end of the resilient bottom member when the prosthetic foot is in an unloaded state; and
a mounting bracket comprising:
an upper member comprising an upper flange, a mating post, and mounting portion configured to attach to the residual limb;
a lower member comprising a mating portion, a lower flange, and a mounting portion configured to attach to the rear end of the resilient top member, wherein the lower flange of the lower member comprises a pair of stops; and
a compression torsion joint coupling the upper member to the lower member and configured to limit vertical movement and torsional movement of the upper member with respect to the lower member, comprising:
an elastomeric ring configured to limit the vertical movement and torsional movement of the upper member with respect to the lower member; and
a compression torsion bumper configured to limit the vertical movement and torsional movement of the upper member with respect to the lower member, wherein the compression torsion bumper contacts the stops to resist torsional movement of the upper member with respect to the lower member.

21. The prosthetic foot of claim 20, wherein the elastomeric ring comprises an upper surface coupled to a channel in the upper flange and a lower surface coupled to a channel in the lower flange; and the compression torsion bumper is coupled to the upper flange of the upper member.

22. The prosthetic foot of claim 20, further comprising a retention system comprising:
a cylindrical sleeve inserted within the mating portion of the lower member and configured to receive the mating post of the upper member to provide smooth vertical and torsional movement between the mating post of the upper member and the mating portion of the lower member; a plug coupled within a lower end of the mating post of the upper member; and a connector coupled to the plug and configured to contact a lower end of the lower member to attach the upper member to the lower member.

* * * * *